United States Patent
Li et al.

(10) Patent No.: US 11,328,391 B2
(45) Date of Patent: May 10, 2022

(54) SYSTEM AND METHOD FOR CONTROLLING NOISE IN MULTI-ENERGY COMPUTED TOMOGRAPHY IMAGES BASED ON SPATIO-SPECTRAL INFORMATION

(71) Applicant: Mayo Foundation for Medical Education and Research, Rochester, MN (US)

(72) Inventors: Zhoubo Li, Libertyville, IL (US); Cynthia H. McCollough, Byron, MN (US); Shuai Leng, Rochester, MN (US); Lifeng Yu, Byron, MN (US); Armando Manduca, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/099,332

(22) PCT Filed: May 8, 2017

(86) PCT No.: PCT/US2017/031539
§ 371 (c)(1),
(2) Date: Nov. 6, 2018

(87) PCT Pub. No.: WO2017/193122
PCT Pub. Date: Nov. 9, 2017

(65) Prior Publication Data
US 2019/0213715 A1  Jul. 11, 2019

Related U.S. Application Data

(60) Provisional application No. 62/332,688, filed on May 6, 2016.

(51) Int. Cl.
*G06T 5/00* (2006.01)
*G06T 5/20* (2006.01)
(Continued)

(52) U.S. Cl.
CPC .............. *G06T 5/002* (2013.01); *A61B 6/032* (2013.01); *A61B 6/482* (2013.01); *A61B 6/5258* (2013.01);
(Continued)

(58) Field of Classification Search
CPC ....... A61B 6/482; A61B 6/032; A61B 6/5258; G06T 5/002; G06T 5/20; G06T 5/50;
(Continued)

(56) References Cited

U.S. PATENT DOCUMENTS 6,018,562 A  1/2000 Willson
9,036,771 B2  5/2015 Yu
(Continued)

FOREIGN PATENT DOCUMENTS

EP    2759983    7/2014

OTHER PUBLICATIONS

Yu, Z. et al. Spectral prior image constrained compressed sensing (spectral PICCS) for photon-counting computed tomography. Physics in Medicine and Biology. 2016;61:6707.
(Continued)

*Primary Examiner* — Nay A Maung
*Assistant Examiner* — Jose M Torres
(74) *Attorney, Agent, or Firm* — Quarles & Brady LLP

(57) ABSTRACT

System and methods are provided for producing computed tomography (CT) images. In some aspects, a method includes obtaining medical image data sets acquired using the multiple energies of irradiating radiation and analyzing the medical image data sets for spatial and spectral features. The method also includes comparing the spatial and spectral
(Continued)

features of the medical image data sets to identify similarities and using the similarities, weighting the medical image data sets to generate images of the subject having reduced noise compared to images of the subject produced from the medical image data sets without weighting.

14 Claims, 14 Drawing Sheets

(51) Int. Cl.
    *G06T 5/50*     (2006.01)
    *G06T 11/00*     (2006.01)
    *A61B 6/03*     (2006.01)
    *A61B 6/00*     (2006.01)
    *G06K 9/62*     (2006.01)
    *G06V 10/75*     (2022.01)

(52) U.S. Cl.
    CPC .............. *G06K 9/6215* (2013.01); *G06T 5/20* (2013.01); *G06T 5/50* (2013.01); *G06T 11/008* (2013.01); *G06T 2200/04* (2013.01); *G06T 2207/10081* (2013.01); *G06T 2207/20021* (2013.01); *G06T 2207/20024* (2013.01); *G06V 10/759* (2022.01)

(58) Field of Classification Search
    CPC ............... G06T 11/008; G06T 2200/04; G06T 2207/20021; G06T 2207/20024; G06T 2207/10081; G06K 9/6215; G06K 2009/6213
    See application file for complete search history.

(56) References Cited

U.S. PATENT DOCUMENTS

| | | | |
|---|---|---|---|
| 9,208,585 B2 | 12/2015 | Leng | |
| 9,754,387 B2 | 9/2017 | Leng | |
| 2004/0101104 A1* | 5/2004 | Avinash | A61B 6/463 378/98.12 |
| 2006/0109949 A1* | 5/2006 | Tkaczyk | A61B 6/032 378/4 |
| 2011/0211057 A1* | 9/2011 | Iwase | G06T 7/33 348/78 |
| 2013/0108013 A1 | 5/2013 | Leng et al. | |
| 2014/0023181 A1* | 1/2014 | Noshi | A61B 6/4241 378/98 |
| 2014/0200447 A1 | 7/2014 | Rousso et al. | |
| 2016/0300368 A1* | 10/2016 | Flohr | G06F 19/321 |
| 2017/0098317 A1* | 4/2017 | Qi | G06T 5/002 |

OTHER PUBLICATIONS

Yuan, R. et al., "Reduced Iodine Load at CT Pulmonary Angiography with Dual-Energy Monochromatic Imaging: Comparison with Standard CT Pulmonary Angiography-A Prospective Randomized Trial," Radiology 262, 290-297 (2012).
Zeng, D., et al. "Spectral CT image restoration via an average image-induced nonlocal means filter." IEEE Transactions on Biomedical Engineering 63.5 (2015): 1044-1057.
International Search Report and Written Opinion dated Sep. 15, 2017 from parent PCT/US17/31539, 19 pages.
Baker ME, et al. Contrast-to-noise ratio and low-contrast object resolution on full-and low-dose MDCT: SAFIRE versus filtered back projection in a low-contrast object phantom and in the liver. American Journal of Roentgenology. 2012;199:8-18.
Boone J.M., "Determination of the presampled MTF in computed tomography," Med Phys 28, 356-360 (2001).
Buades, A. et al, "A review of image denoising algorithms, with a new one," Multiscale Model Sim 4, 490-530 (2005).
Buades, A.et al. "Non-local means denoising." Image Processing On Line 1 (2011): 208-212.
Buerke, B. et al, "Dual-Energy CTA with Bone Removal for Transcranial Arteries: Intraindividual Comparison with Standard CTA without Bone Removal and TOF-MRA," Acad Radiol 16, 1348-1355 (2009).
Chandarana, H. et al, "Iodine Quantification With Dual-Energy CT: Phantom Study and Preliminary Experience With Renal Masses," Am J Roentgenol 196, W693-W700 (2011).
Choi, H.K. et al, "Dual energy computed tomography in tophaceous gout," Ann Rheum Dis 68, 1609-1612 (2009).
Clark, D.P. et al, "Spectral diffusion: an algorithm for robust material decomposition of spectral CT data," Phys Med Biol 59, 6445-6466 (2014).
Dai, J., et al. "Multichannel nonlocal means fusion for color image denoising." IEEE Transactions on Circuits and Systems for Video Technology 23.11 (2013): 1873-1886.
Dolly S, et al. Practical considerations for noise power spectra estimation for clinical CT scanners. Journal of Applied Clinical Medical Physics. 2016;17:5841.
Dong, X. et al, "Combined iterative reconstruction and image-domain decomposition for dual energy CT using total-variation regularization," Med Phys 41, 051909 (2014).
European Patent Office, Extended European Search Report and European Search Opinion for application 17793542.6, dated Nov. 6, 2019.
Glazebrook, K.N. et al, "Identification of Intraarticular and Periarticular Uric Acid Crystals with Dual-Energy CT: Initial Evaluation," Radiology 261, 516-524 (2011).
Goenka AH, et al. Effect of reduced radiation exposure and iterative reconstruction on detection of low-contrast low-attenuation lesions in an anthropomorphic liver phantom: an 18-reader study. Radiology. 2014;272:154-163.
Graser, A. et al, "Dual energy CT characterization of urinary calculi: Initial in vitro and clinical experience," Invest Radiol 43, 112-119(2008).
Gutjahr, R. et al, "Human Imaging With Photon Counting-Based Computed Tomography at Clinical Dose Levels Contrast-to-Noise Ratio and Cadaver Studies," Invest Radiol Invest Radiol. 2016;51:421-429.
Harms J, et al. Noise suppression for dual-energy CT via penalized weighted least-square optimization with similarity-based regularization. Medical physics. 2016;43:2676-2686.
Johnson, T.R. et al, "Material differentiation by dual energy CT: initial experience," Eur Radiol 17, 1510-1517 (2007).
Kalender, W.A. et al, "An algorithm for noise suppression in dual energy CT material density images," IEEE Trans Med Imaging 7, 218-224 (1988).
Kappler, S. et al, "First results from a hybrid prototype CT scanner for exploring benefits of quantum-counting in clinical CT," vol. 8313 (2012), pp. 83130X-83130X-83111.
Leng, S. et al, "Noise reduction in spectral CT: Reducing dose and breaking the trade-off between image noise and energy bin selection," Med Phys 38, 4946-4957 (2011).
Li K, et al. Statistical model based iterative reconstruction (MBIR) in clinical CT systems. Part II. Experimental assessment of spatial resolution performance. Medical physics. 2014;41:071911.
Li, Y. et al, "Iodine quantification with dual-energy CT: phantom study and preliminary experience with VX2 residual tumour in rabbits after radiofrequency ablation," Brit J Radiol 86, 20130143 (2013).
Li, Z. et al, "Image-based material decomposition with a general volume constraint for photon-counting CT," in SPIE Medical Imaging (International Society for Optics and Photonics, 2015), pp. 94120T-94120T.
Li, Z. et al., "A robust noise reduction technique for time resolved CT," Med. Phys. 43 (1), Jan. 2016.
Li, Z., et al. "Adaptive nonlocal means filtering based on local noise level for CT denoising." Medical physics 41.1 Dec. 31, 2013, p. 011908.
Li, Z., et al. "An effective noise reduction method for multi-energy CT images that exploit spatio-spectral features." Medical physics 44.5 (2017): 1610-1623.

(56) References Cited

OTHER PUBLICATIONS

Macovski, A. et al, "Measurement-Dependent Filtering: A Novel Approach to Improved SNR," IEEE Trans Med Imaging 2, 122-127 (1983).
Manhart, M. et al, "Guided noise reduction for spectral CT with energy-selective photon counting detectors," Proc CT Meet, 91-94 (2014).
Manjon JV, et al. Proc MIUA. TINA; Manchester: 2007. Multispectral MRI De-noising Using Non-Local Means.
McCollough CH, et al. Degradation of CT low-contrast spatial resolution due to the use of iterative reconstruction and reduced dose levels. Radiology. 2015;276:499-506.
McCollough, CH et al, "Dual- and Multi-Energy CT: Principles, Technical Approaches, and Clinical Applications," Radiology 276, 637-653 (2015).
Nicolaou, S. et al, "Dual-Energy CT as a Potential New Diagnostic Tool in the Management of Gout in the Acute Setting," Am J Roentgenol 194, 1072-1078 (2010).
Niu, T.Y. et al, "Iterative image-domain decomposition for dual-energy CT," Med Phys 41, 041901 (2014).
Pan N, et al. Improving the image quality of spectral CT volume rendering. 24th International Conference Image and Vision Computing; New Zealand. 2009. pp. 203-208.
Pelc N.J., "Recent and future directions in CT imaging," Ann Biomed Eng 42, 260-268 (2014).
Primak, A.N. et al, "Noninvasive differentiation of uric acid versus non-uric acid kidney stones using dual-energy CT," Acad Radiol 14, 1441-1447 (2007).
Roessl, E. et al, "K-edge imaging in x-ray computed tomography using multi-bin photon counting detectors," Phys Med Biol 52, 4679-4696 (2007).
Schindera ST, et al. Iterative reconstruction algorithm for CT: can radiation dose be decreased while low-contrast detectability is preserved? Radiology. 2013;269:511-518.
Schlomka, J.P. et al, "Experimental feasibility of multi-energy photon-counting K-edge imaging in pre-clinical computed tomography," Phys Med Biol 53, 4031-4047 (2008).
Schmidt TG. Optimal "image-based" weighting for energy-resolved CT. Medical Physics. 2009;36:3018-3027.
Shikhaliev P.M., "Computed tomography with energy-resolved detection: a feasibility study," Phys Med Biol 53, 1475-1495 (2008).
Siewerdsen, J.H. et al, "A framework for noise-power spectrum analysis of multidimensional images," Med Phys 29, 2655-2671 (2002).
Taguchi, K. et al, "Vision 20/20: Single photon counting x-ray detectors in medical imaging," Med Phys 40, 100901 (2013).
Xi, Y. et al, "United Iterative Reconstruction for Spectral Computed Tomography," IEEE Trans Med Imaging 34, 769-778 (2015).
Yu L, et al. Technical Note: Measuring contrast-and noise-dependent spatial resolution of an iterative reconstruction method in CT using ensemble averaging. Medical physics. 2015;42:2261-2267.
Yu, L. et al, "Virtual monochromatic imaging in dual-source dual-energy CT: radiation dose and image quality," Med Phys 38, 6371-6379 (2011).
Yu, Z. et al, "Evaluation of conventional imaging performance in a research whole-body CT system with a photon-counting detector array," Phys Med Biol 61, 1572-1595 (2016).
Yu, Z. et al, "Initial results from a prototype whole-body photon-counting computed tomography system," in SPIE Medical Imaging (International Society for Optics and Photonics, 2015), pp. 94120W-94120W.
Yu, Z. et al, "Low-dose performance of a whole-body research photon-counting CT scanner," in SPIE Medical Imaging, vol. 9783 (International Society for Optics and Photonics, San Diego, California, United States, 2016).

\* cited by examiner

SYSTEM AND METHOD FOR CONTROLLING NOISE IN MULTI-ENERGY COMPUTED TOMOGRAPHY IMAGES BASED ON SPATIO-SPECTRAL INFORMATION

CROSS-REFERENCE TO RELATED APPLICATIONS

This application is a 371 U.S. National Phase application of PCT/US2017/031539, filed May 8, 2017, which is based on, claims priority to, and incorporates herein by reference in its entirety, U.S. Provisional Application Ser. No. 62/332,688, filed May 6, 2016, and entitled, "SYSTEM AND METHOD FOR CONTROLLING NOISE IN MULTI-ENERGY COMPUTED TOMOGRAPHY IMAGES BASED ON SPATIO-SPECTRAL INFORMATION."

GOVERNMENT FUNDING

This invention was made with government support under EB016966 awarded by the National Institutes of Health. The government has certain rights in the invention.

BACKGROUND

The present disclosure relates to medical imaging. More particularly, the present disclosure relates to systems and methods for controlling radiation doses delivered and noise levels in resulting images when performing imaging processes using ionizing radiation, for example, by performing image-domain noise reduction using multi-energy CT (MECT) data.

In a computed tomography system, an x-ray source projects a beam that is collimated to lie within an X-Y plane of a Cartesian coordinate system, termed the "imaging plane." The x-ray beam passes through the object being imaged, such as a medical patient or other non-medical patient or object, such as in industrial CT imaging, and impinges upon an array of radiation detectors. The intensity of the transmitted radiation is dependent upon the strength of the unattenuated beam emerging from the x-ray source (i.e. the applied radiation dose) and the attenuation of the x-ray beam by the object. Each detector produces a separate electrical signal that is a measurement of the attenuated beam. The attenuation measurements from all the detectors are acquired separately to produce the transmission profile at a particular view angle.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view", and a "scan" of the object comprises a set of views acquired at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique, however, other image reconstruction processes are also well known. This process converts the attenuation measurements from a scan into integers called "CT numbers" or "Hounsfield units", which are used to control the brightness of a corresponding pixel on a display.

The drastically increased use of CT in modern clinical settings has generated serious public health concerns regarding the cancer risks associated with the radiation exposure from CT. The current guiding principle in CT clinical practice is to use radiation dose levels as low as reasonably achievable while maintaining acceptable diagnostic accuracy. However, lowering radiation dose alone generally produces a noisier image and may seriously degrade diagnostic performance. Many algorithms have been proposed for controlling noise in CT, and these can be broadly categorized into 3 major types: projection space, image space, and iterative reconstruction.

Projection space techniques, which work on either the raw projection data or the log-transformed sinogram, attempt to reduce noise in the projection data domain prior to image reconstruction. In general, these techniques have the advantage that noise properties in projection space are fairly well understood. One potential drawback of projection-based methods is that they may result in some loss of image sharpness due to the fact that edges in projection data are not well-defined.

Image-space denoising involves applying linear or non-linear filters directly to the reconstructed images. Most such techniques (e.g. bilateral filtering, total variation denoising, non-local means denoising, and k-SVD denoising) take advantage of the strong structural and statistical properties of objects in image space (e.g. sharp edges, similarities between neighboring pixels). In CT, they can be implemented directly and without access to the raw data. However, CT noise in image space is difficult to model accurately and has strong spatial variations and correlations. It can therefore be more difficult for such techniques to achieve an optimal tradeoff between denoising and blurring or artifacts, or to get consistent performance across an entire scan volume.

Iterative reconstruction (IR) techniques are more accurately considered reconstruction rather than denoising techniques, and take advantage of statistical assumptions about the noise properties in projection space and structure in image space. IR techniques require access to the raw data and accurate knowledge of the details of the scanner geometry, photon statistics, data-acquisition and correction physics, thus they are highly dependent on specific scanner models. True IR is very computationally intensive (e.g., several hours per data set), which has prevented fast clinical application to date, although software methods and hardware methods have been investigated to accelerate the iterative procedure. Due to the extremely high computational load of true IR, hybrid techniques have recently been developed that attempt to gain many of the benefits of true IR with much lower computational load (e.g. Sinogram AFirmed Iterative REconstruction (SAFIRE) from Siemens).

Non-local means (NLM) denoising is an effective image denoising strategy that exploits the inherent redundant information present in most images. NLM generalizes the notion of finite spatial differences and utilizes a measure of difference between nearby image patches to estimate underlying image structure. This allows NLM to preserve a high degree of image texture and fine detail. However, the standard NLM algorithm uses a uniform filtering strength to denoise the image, while in CT images the noise level varies significantly within and across slices. Therefore, applying NLM filtering to CT images using a global filtering strength cannot achieve optimal denoising performance.

Some have estimated the local noise of CT images, and denoised the images, using a modified NLM algorithm that is adaptive to local variations in noise, for example, variations in noise levels. One such technique is described in U.S. Pat. No. 9,036,771. These systems and methods work well. However, given the importance of dose control to and the diversity of uses for CT imaging in clinical medicine, additional and specialized techniques for controlling dose and noise are needed, particularly, for multi-energy images.

Therefore, it would be desirable to have additional systems and methods for controlling or managing dose and noise in a broader range of clinical settings.

SUMMARY

The present disclosure provides systems and methods that overcome the aforementioned drawbacks by providing a multi-energy non-local means (MENLM) technique that can use the redundant information in multi-energy CT (MECT) data to control noise within CT images. For example, a system and method is provided to use spatio-spectral features across MECT images to determine similarity between pixels and perform a similarity evaluation that is more robust to image noise than would otherwise be possible, all while maintaining spatial and energy resolution.

In accordance with one aspect of the disclosure, a method is provided for producing an image acquired by measuring multiple energies of the photon radiation irradiating a subject. The method includes obtaining medical image data sets acquired using the multiple energies of irradiating radiation and analyzing the medical image data sets for spatial and spectral features. The method also includes comparing the spatial and spectral features of the medical image data sets to identify similarities and using the similarities, weighting the medical image data sets to generate images of the subject having reduced noise compared to images of the subject produced from the medical image data sets without weighting.

In accordance with another aspect of the disclosure, a computed tomography (CT) imaging system is provided that includes at least one x-ray source configured to emit x-rays at one or more energy levels toward an object to be imaged and at least one detector configured to receive x-rays that are attenuated by the object. The CT imaging system also includes a data acquisition system (DAS) connected to the at least one detector to receive an indication of received x-rays at multiple energy levels and a computer system coupled to the DAS to receive the indication of the received x-rays at multiple energy levels. The computer system is programmed to obtain medical image data sets acquired using the multiple energies of irradiating radiation and analyze the medical image data sets for spatial and spectral features. The computer system is also configured to compare the spatial and spectral features of the medical image data sets to identify similarities and use the similarities, weighting the medical image data sets to generate images of the subject having reduced noise compared to images of the subject produced from the medical image data sets without weighting.

In accordance with yet another aspect of the disclosure, a method for producing computed tomography (CT) images is provided. The method includes steps of receiving medical image data sets acquired at multiple energies using a CT system, and reconstructing at least one image using the medical image data sets. The method also includes performing a similarity evaluation based on spatial and spectral features for each selected pixel in the at least one image using pixels in a search window, and filtering each selected pixel in the at least one image according to the similarity evaluation to produce a plurality of filtered pixels. The method further includes generating at least one filtered image using the plurality of filtered pixels.

In accordance with yet another aspect of the disclosure, a computed tomography (CT) imaging system is provided that includes at least one x-ray source configured to emit x-rays at one or more energy levels toward an object to be imaged and at least one detector configured to receive x-rays that are attenuated by the object. The CT imaging system also includes a data acquisition system (DAS) connected to the at least one detector to receive an indication of received x-rays at distinct energy channels and a computer system coupled to the DAS to receive the indication of the received x-rays at distinct energy channels. The computer system is programmed to reconstruct at least one image using image data sets each corresponding to the distinct energy channels, and perform a similarity evaluation based on spatial and spectral features for each selected pixel in the at least one image using pixels in a search window. The computer system is also programmed to filter each selected pixel in the at least one image according to the similarity evaluation to produce a plurality of filtered pixels, and generate at least one filtered image using the plurality of filtered pixels.

In accordance with yet another aspect of the disclosure, a method for producing computed tomography (CT) images is provided. The method includes receiving medical image data sets acquired at multiple energies using a CT system, and analyzing the medical image data sets to determine spatial and spectral information. The method also includes performing a similarity evaluation using the spatial information and spectral information, and based on the similarity evaluation, filtering each selected pixel in at least one image generated from the medical image data sets to produce a plurality of filtered pixels. The method further includes generating at least one filtered image using the plurality of filtered pixels.

Various other features of the present invention will be made apparent from the following detailed description and the drawings.

DETAILED DESCRIPTION

Figure 1A:
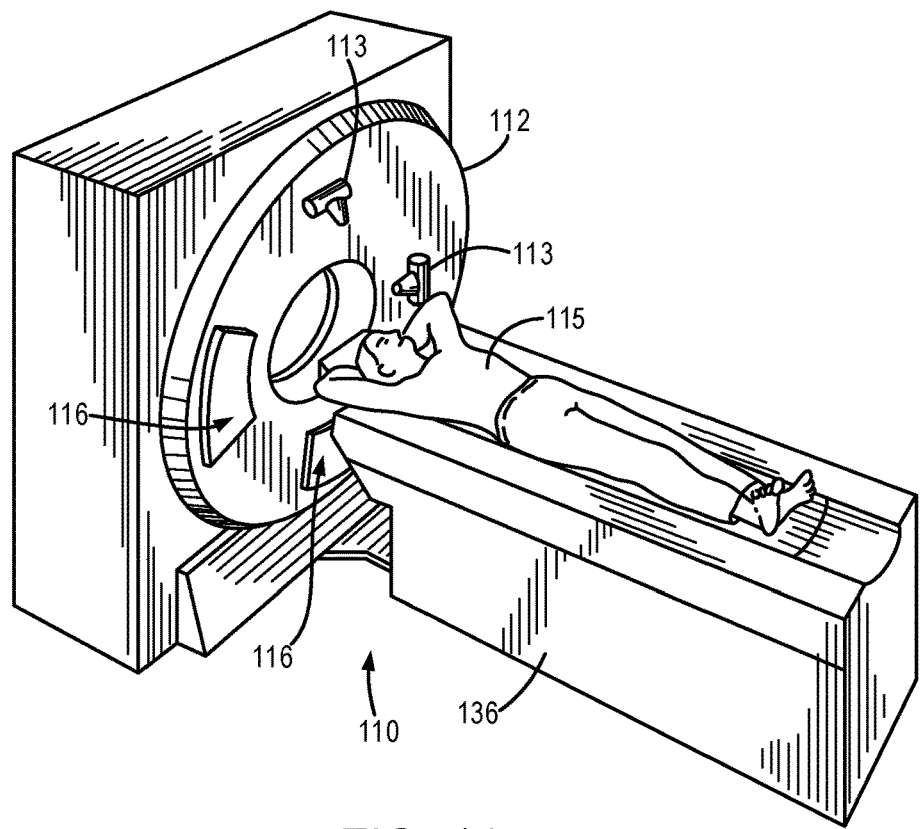
FIG. 1A is a schematic of a computed tomography (CT) imaging system, in accordance with aspects of the present disclosure.

Multi-energy CT (MECT) has gained increasing interest in clinical medicine and can be performed using both multi-source and single-source CT systems. Within the general category of MECT, some particular clinical applications have gained substantial acceptance. For example, dual-energy CT has demonstrated its value in clinical applications, such as iodine quantification, monochromatic imaging, bone removal, kidney stone characterization, and gout imaging. Photon counting detector-based CT (PCCT) may further benefit clinical CT by offering improved energy resolution, higher dose efficiency, and better signal-to-noise (SNR) properties.

Various algorithms have been proposed to effectively control image noise for MECT to improve image quality and/or quantitative accuracy. Since MECT images acquired at different energies are usually perfectly registered in the image domain, pixels at the same spatial coordinates represent exactly the same object and are associated with same structures, albeit with different contrast levels. Hence, one may exploit data redundancies in the energy domain to achieve noise reduction.

S. Leng, L. F. Yu, J. Wang, J. G. Fletcher, C. A. Mistretta, C. H. McCollough, "Noise reduction in spectral CT: Reducing dose and breaking the trade-off between image noise and energy bin selection," Med Phys 38, 4946-4957 (2011), which is incorporated herein by reference, proposed an energy-domain filtration method that used a composite image with much lower noise to effectively reduce noise in energy bin-based images to that of the composite image. The same concept has also been applied in other noise reduction algorithms, and can occur in either image-domain or projection-domain, or as iterative approaches, as described in M. Manhart, R. Fahrig, J. Hornegger, A. Doerfler, A. Maier, "Guided noise reduction for spectral CT with energy-selective photon counting detectors," Proc CT Meet, 91-94 (2014). Or Y. Xi, Y. Chen, R. B. Tang, J. Q. Sun, J. Zhao, "United Iterative Reconstruction for Spectral Computed Tomography," IEEE Trans Med Imaging 34, 769-778 (2015), each of which is incorporated herein by reference.

In addition to exploiting features in the energy domain between the original MECT images, noise reduction has also been performed on secondary images generated from distinct multi-energy measurements. W. A. Kalender, E. Klotz, L. Kostaridou, "An algorithm for noise suppression in dual energy CT material density images," IEEE Trans Med Imaging 7, 218-224 (1988), which is incorporated herein by reference, developed a method utilizing noise correlations in material specific images to reduce noise. T. G. Schmidt, "Optimal "image-based" weighting for energy-resolved CT," Med Phys 36, 3018-3027 (2009) presented a method to maximize the contrast to noise (CNR) of a mixed image by blending images from separate energy bin-based images. Recently, noise reduction for MECT was also performed together with quantitative basis material decomposition by iterative methods with smoothness regularization of basis material density, such as described by T. Y. Niu, X. Dong, M. Petrongolo, L. Zhu, "Iterative image-domain decomposition for dual-energy CT," Med Phys 41, 041901 (2014)., X. Dong, T. Y. Niu, L. Zhua, "Combined iterative reconstruction and image-domain decomposition for dual energy CT using total-variation regularization," Med Phys 41, 051909 (2014)., and D. P. Clark, C. T. Badea, "Spectral diffusion: an algorithm for robust material decomposition of spectral CT data," Phys Med Biol 59, 6445-6466 (2014), each of which is incorporated herein by reference.

As will be described, the present disclosure provides a different approach for generating MECT images. In particular, intrinsic redundant information in MECT images is exploited herein by searching for similar spatial and spectral features to reduce image noise while preserving spatial and energy resolution. The technique can utilize reconstructed images directly to achieve fast noise reduction. Filtered images generated in accordance with the present disclosure can not only improve the detection of relevant anatomical information but also reduce the noise magnification that occurs in the post-processing steps.

That is, as will be described, the present disclosure provides an approach that stands in contrast to traditional noise reduction methods in CT. For example, energy-domain noise reduction uses weighting calculation and filtering performed only in the energy domain and requires a composite image with low noise to operate effectively. To this end, the effectiveness of the noise reduction is specifically determined by the noise level in the composite image, which is a substantial limitation of the method. Also, conventional non-local means (cNLM) or adaptive non-local means (aNLM) techniques utilize weighting calculations and filtering performed only in the spatial domain and, thereby, ignoring the signal correlations in the energy domain. The weighting calculation is based on the similarity evaluation of only spatial features. As such, the accuracy of such spatially-based similarity calculations is very susceptible to image noise level. This is a problem reported numerous times in the literature and it limits the noise reduction capability of cNLM and aNLM.

In contrast, the present disclosure provides systems and methods that are not reliant on the simple application of cNLM to multi-energy images. Rather, weighting can be determined by determining a similarity between features in both spatial and energy domain, whereas filtering may be applied only in the spatial domain. The features in energy domain can be very different from the image noise and, hence, the systems and methods of the present disclosure improve the robustness of similarity calculation over traditional methods. For example, the signal of iodinated blood can vary with tens or hundreds of CT numbers between measurements at different energies. This results in very sharp features that cannot be disguised by image noise. This weight calculation can be also sensitive to small changes in material concentrations. Even small changes will result in differences of signal at different measurements, which helps to preserve small features, even in challenging low-contrast objects.

Figure 1B:
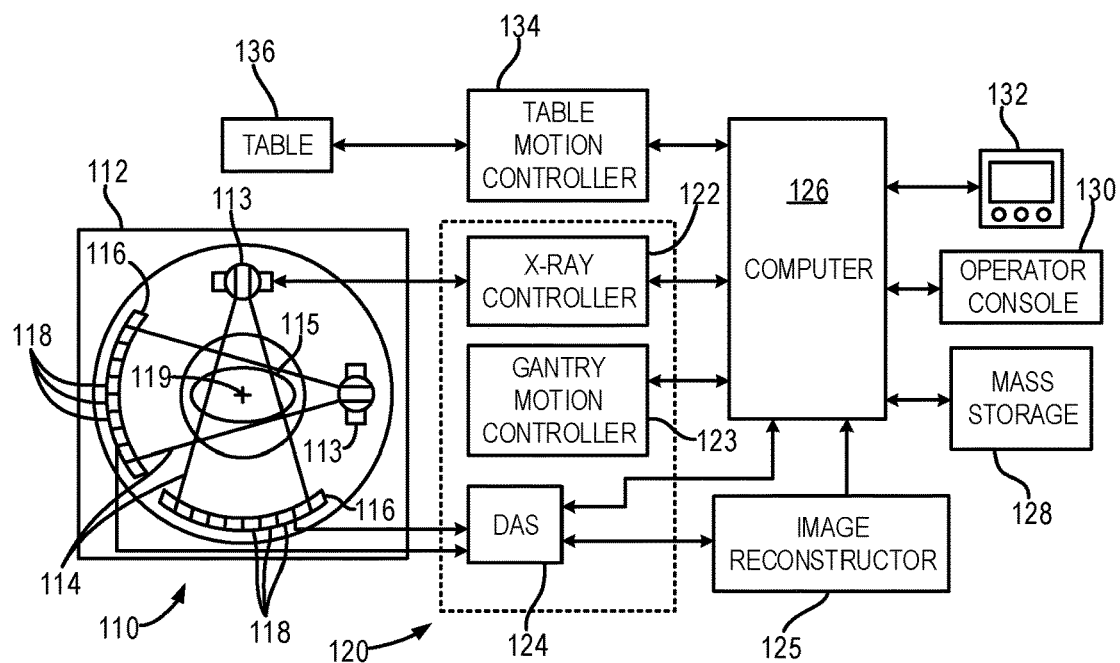
FIG. 1B is block schematic diagram of the CT imaging system of FIG. 1A.

With initial reference to FIGS. 1A and 1B, a computed tomography (CT) imaging system 110 includes a gantry 112 representative of at least a "multi-energy" CT system. In the illustrated example, the gantry 112 has a pair of x-ray sources 113 that each projects a respective fan beam or cone beam of x-rays 114 toward a detector array 116 on the opposite side of the gantry 112. Such illustration of a "dual source" system is non-limiting. For example, the systems and methods of the present invention may likewise be used with traditional "single source" CT systems that are controlled to effectuate a multi-energy imaging process. The detector array 116 may include traditional, "energy integrating" detectors or may include "photon counting" and/or "energy discriminating" detectors. In any case, the detector array 116 is formed by a number of detector elements 118 that together sense the projected x-rays that pass through a medical patient or subject 115. During a scan to acquire x-ray projection data, the gantry 112 and the components mounted thereon rotate about a center of rotation 119 located within the subject 115 to acquire CT data.

The rotation of the gantry 112 and the operation of the x-ray source(s) 113 are governed by a control mechanism 120 of the CT system 110. The control mechanism 120 includes an x-ray controller 122 that provides power and timing signals to the x-ray source(s) 113 and a gantry motor controller 123 that controls the rotational speed and position of the gantry 112. A data acquisition system (DAS) 124 in the control mechanism 120 samples analog data from detector elements 118 and converts the data to digital signals for subsequent processing. An image reconstructor 125, receives sampled and digitized x-ray data from the DAS 124 and performs high speed image reconstruction. The reconstructed image is applied as an input to a computer 126 that stores the image in a mass storage device 128.

The computer 126 also receives commands and scanning parameters from an operator via, for example, console 130. An associated display 132 allows the operator to observe the reconstructed image and other data from the computer 126. The operator-supplied commands and parameters are used by the computer 126 to provide control signals and information to the DAS 124, the x-ray controller 122, and the gantry motor controller 123. In addition, the computer 126 can operate a table motor controller 134 that controls a motorized table 136 to position the patient 115 in the gantry 112.

The present disclosure provides an approach to exploiting the intrinsic redundant information in MECT images by searching for similar spatio-spectral features to reduce image noise while preserving spatial and energy resolution. The technique can utilize reconstructed images directly to achieve fast noise reduction. The images can be used to improve the detection of relevant anatomical information and also reduce the noise magnification that occurs in post-processing steps.

Figure 2A:
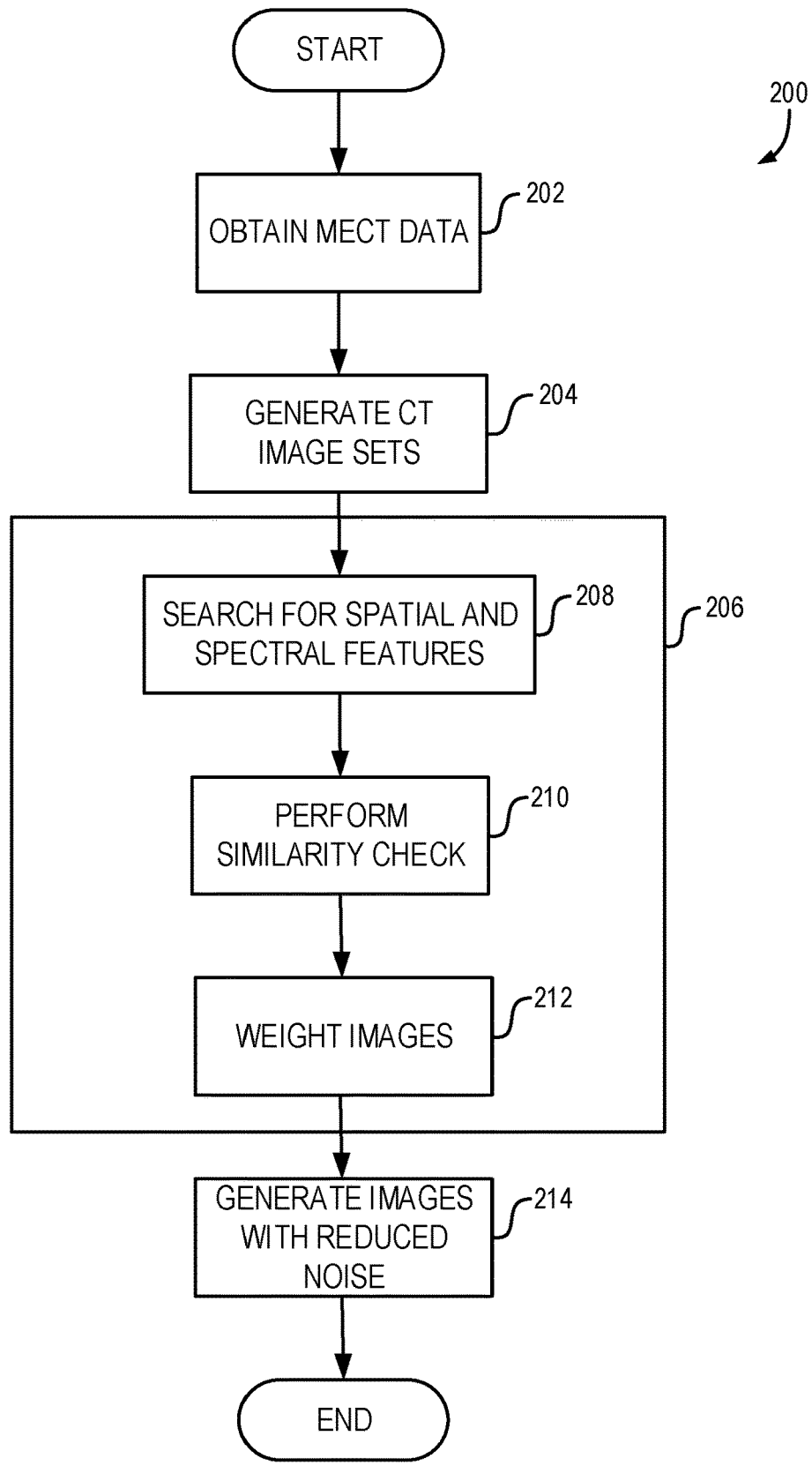
FIG. 2A is a flowchart setting forth steps of a process, in accordance with aspects of the present disclosure.

Specifically, referring to FIG. 2A, a process 200 in accordance with the present disclosure includes obtaining MECT data at process block 202. This may include performing an imaging process using a CT system, such as described above with respect to FIGS. 1A and 1B, or simply accessing stored MECT data. Once the MECT data is acquired at process block 202, the MECT data 202 may be reconstructed to generate CT image data sets at process block 204.

As generally illustrated by block 206, an analysis process is then performed. In particular, as will be described, a state-of-the-art, edge-preserving noise reduction algorithm is provided that incorporates a non-local means (NLM) approach. NLM is described, for example, in A. Buades, B. Coll, J. M. Morel, "A review of image denoising algorithms, with a new one," Multiscale Model Sim 4, 490-530 (2005), which is incorporated herein by reference. As will be described, the present disclosure uses NLM to search for similar pixels at process block 208 in an original image and then, if the identified pixels are determined to be sufficiently similar at process block 210, a weighted average of such pixels is performed at process block 212 to achieve noise reduction. More particularly, the similarity between the pixel to be filtered and all other pixels can be quantitatively determined by the summed square difference (SSD) between the features associated with the pixels at process block 210. Pixels with lower SSD yield higher similarity and, hence, can receive higher weight at process block 212. As will be demonstrated, the result of this process 200 is to, thereby, generate images with reduced noise at process block 214, as compared to non-filtered/weighted image combinations of MECT data.

The accurate evaluation of similarity between pixels has a substantial impact on the noise reduction performance. Hence, a preferred feature definition may carefully consider the characteristics of the images to be filtered. In conventional NLM algorithms, two dimensional (2D) spatial patches are used as features to search for the similarity. For three dimensional (3D) data, such as volumetric CT images, spatial features can be extended to 3D blocks to calculate similarity.

Though the initial identification of pixels is performed at process block 208 using a search for spatial features, the similarity measurement at process block 210 may not be limited to spatial features alone, especially for high-dimensional images. In time-resolved CT images, for example, the partial temporal profile of a pixel can be used to effectively utilize redundant information in both spatial and temporal domains, and is robust to patient motion, as described in Li, et al., "A robust noise reduction technique for time resolved CT," Med. Phys. 43 (1), January 2016, which is incorporated herein in its entirety. Similarly, incorporation of the energy and spatial characteristics of MECT images across 3D spatial domain and multiple energy channels is preformed to achieve a desired noise reduction.

Thus, referring again to FIG. 2A, the method considers the spatial features together with spectral features at process block 208 to improve the robustness of similarity calculations performed at process block 210. As will be described, this can be done in the image domain because the pixels at distinct energy channels are perfectly registered in the image domain.

In particular, the pixel values (or CT numbers) in CT images measure the effective linear attenuation coefficient (LAC) of a type of material for a given incident X-ray spectrum and are a function of the material's effective atomic number and density. In conventional CT, a material's LAC is only evaluated at a single energy spectrum. Therefore, materials with different compositions and densities can have similar LAC values at certain X-ray energy spectrum. However, in MECT, LAC measurements can be acquired at two or more different energy spectra to build an energy profile (or spectral features) for each pixel.

Figure 3A:
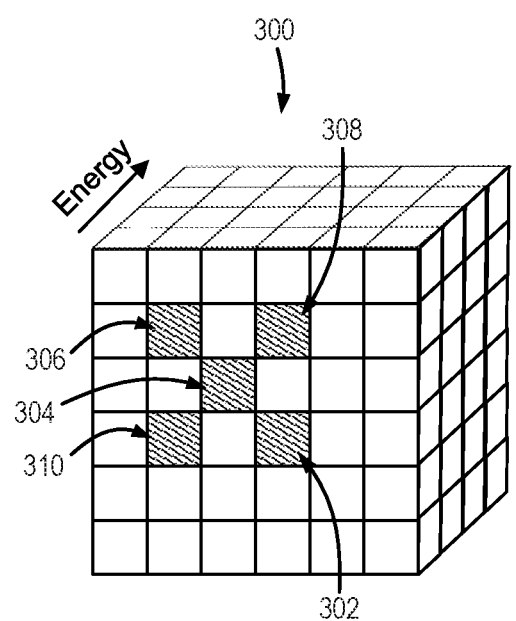
FIG. 3A is a graphic showing an illustration of pixels in multi-energy CT images, in accordance with the present disclosure.

The energy profile can be exploited for noise reduction. Referring to FIG. 3A, consider a set of 2D MECT images acquired at 4 different X-ray energies that are stacked together to form a 3D volume 300. Each block in a plane represents a pixel 302, 304, 306, 308, 310 evaluated at certain spatial location and X-ray energy. The 4 pixels values associated with the same spatial location form an energy profile, as illustrated in the curves in FIGS. 3B (302, 304, 306) and 3C (304, 308, 310).

Figure 3B:
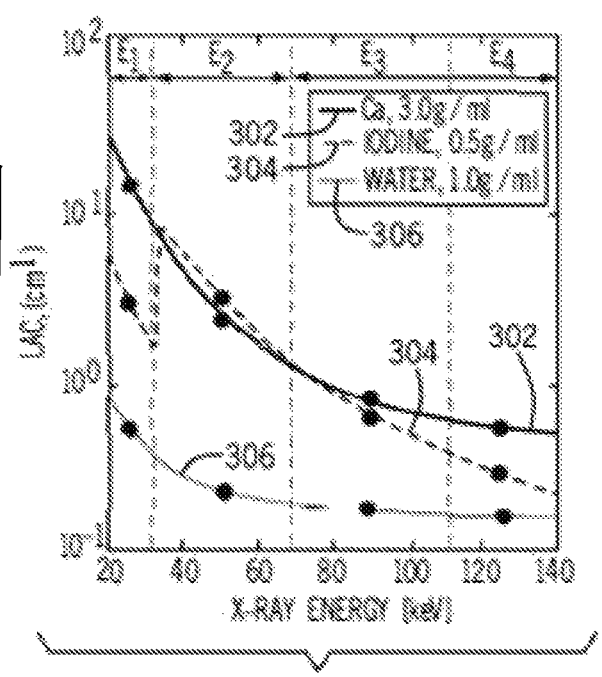
FIG. 3B is a graph illustrating that pixels shown in FIG. 3A with different material compositions and densities can have distinct spectral features that may be used in an evaluation, in accordance with aspects of the present disclosure.
Figure 3C:
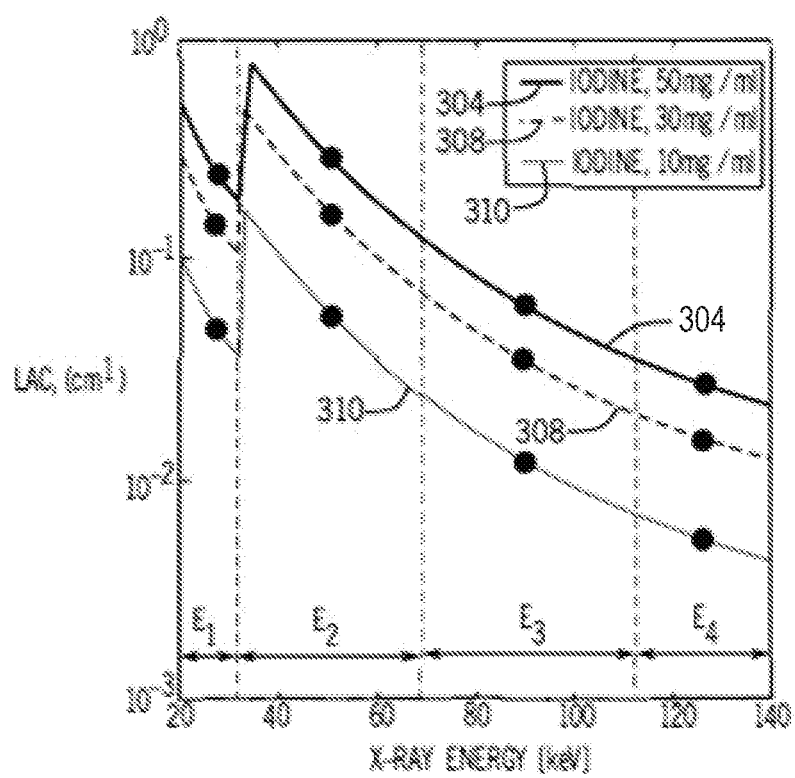
FIG. 3C is a graph illustrating that pixels shown in FIG. 3A with similar material compositions and different densities can have distinct spectral features that may be used in an evaluation, in accordance with aspects of the present disclosure.

Although different materials can have similar LAC values at a certain energy (e.g. calcium 302 and iodine 304 in energy channels E2 and E3, FIG. 3B), they can be distinguished by their distinct energy profiles, which allows material differentiation and also pixel similarity evaluation. The same principle can also be applied to separate a given material with different densities because the differences in material densities yield differences in LACs in measurements at all X-ray energies, such as illustrated in FIG. 3C, which shows that different concentrations of iodine (e.g. iodine 304, 308, and 310) can be differentiated. Hence, a small difference in density between two pixels can yield a large difference in the SSD between the two energy profiles, which can be beneficial for preserving features with small variations in intensity (or low contrast).

Figure 4:
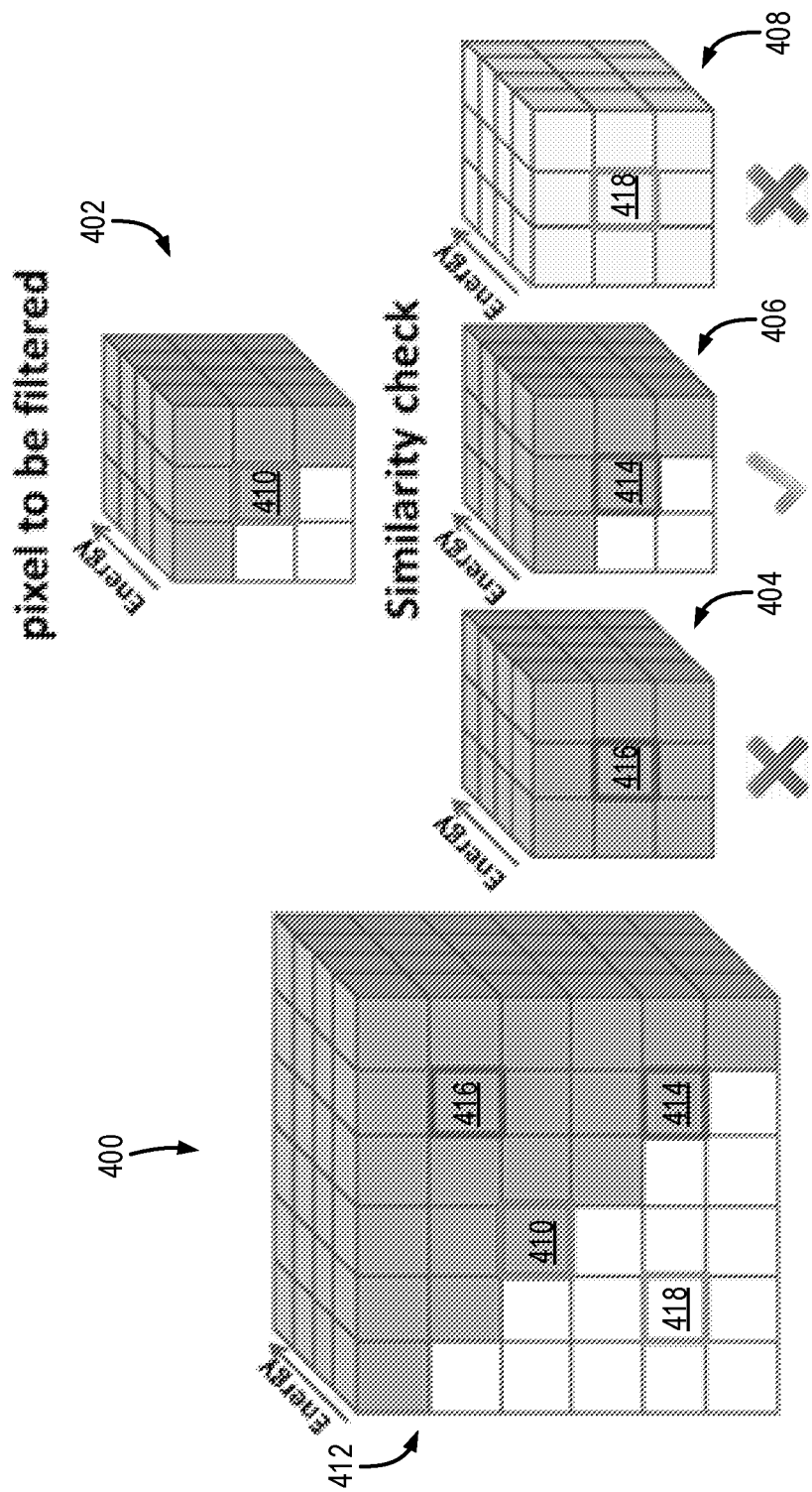
FIG. 4 is a graphic illustration of a process for exploiting spatial features to control noise and preserve edges in filtering, in accordance with aspects of the present disclosure.

With respect to spectral features, NLM can be adapted in accordance with the present disclosure to be applied to the MECT data (i.e., MENLM). To illustrate this, FIG. 4 shows a block of pixels 400 assembled using an MECT dataset. For simplicity, this example shows a MECT dataset that includes a 2D image acquired at multiple energies. It may be readily appreciated that the present approach may be extended to include MECT datasets having multiple 2D images, or one or more 3D images acquired at multiple energies, as well as images acquired at multiple time points. In this regard, the MECT dataset may include a multi-dimensional dataset having spatial, energy and temporal domain information.

In the example of FIG. 4, the NLM, as adapted, can extract the spatial feature associated with each pixel (e.g. 3×3 patches in plane in the spatial domain) and stacks the 2D patch at different energies to form a 3D block 402, 404, 406, 408. That is, the different spatial features in the 3×3 patches are combined with energy profiles to perform a similarity calculation, making the similarity evaluation robust to image noise. In the example illustrated in FIG. 4, when filtering a given pixel 410 on an edge 412, the present approach allows for detecting pixels 414 that are similarly located on an edge and exclude unlike ones 416, 418. Thus, the pixel similarity for a center pixel 410 of a given block 402 is evaluated by calculating the SSDs between different blocks 404, 406, 408 associated with the center pixels 416, 414, 418. In MECT, edges, such as subtle anatomical structures, may not be well defined due to high image noise. The present disclosure can utilize the core concept of conventional NLM algorithms, which exploit spatial features to achieve noise reduction and preserve edges, but enhance this with the use of spectral features.

The difference in image noise levels in distinct energy channels can also be considered in order to correctly evaluate the similarity between pixels. Energy channels associated with higher noise can be weighted less for the similarity calculation at step 212 of FIG. 2A, and vice versa. In particular, a non-limiting example algorithm can be described by the following equation:

$$I'(i_0, e_0) = \frac{\sum_{i \in \Omega} \left( I(i, e_0) \exp\left(-\frac{1}{EW_P^3 h^2}\left(\Sigma_{\delta \in P} \sum_{e=1}^{E} \left(\frac{[I(i+\delta, e) - I(i_0+\delta, e)]^2}{\sigma_e^2}\right)\right)\right)\right)}{\sum_{i \in \Omega} \exp\left(-\frac{1}{EW_P^3 h^2}\left(\Sigma_{\delta \in P} \sum_{e=1}^{E} \left(\frac{[I(i+\delta, e) - I(i_0+\delta, e)]^2}{\sigma_e^2}\right)\right)\right)}; \quad (1)$$

where $I'(i_0, e_0)$ is the filtered pixel value at spatial coordinate $i_0$ measured in energy channel $e_0$, $I(i, e_0)$ are the pixel intensities in the original images measured in the same energy channel $\Omega$ is the search window in the spatial domain, which may be a 3d block with equal dimension $W_\Omega$ in all 3 dimensions in space so that it contains $W_\Omega^3$ pixels. Also, $\delta$ is the spatial offset of the evaluated pixel in the spatial feature P, which may be a 3d block with equal dimension $W_P$ in all 3 dimensions in space so that it contains $W_P^3$ pixels. Further, E is the length of the energy profile used for the similarity evaluation. Hence, the contribution of each pixel I at energy $e_0$ to filtering can be determined by calculating the mean square difference between two 4d blocks (3d spatial+1d energy) centered at the spatial location of $i_0$ and i. Thus, $\sigma_e^2$ represents the image noise variance in the energy channel e and may be manually determined by ROI measurements in a homogenous region in the original images or automatically estimated.

In this way, the similarity can be determined by using multi-energy measurements, but the averaging may only be performed in distinct energy channels to avoid possible signal leakage across different energy channels. The exponential function in the formula can be used to scale the weight within the range [0, 1]. Finally, a weighted average of all pixels in the spatial search window yields the filtered pixel value. In this, h is a parameter used to control the amount of noise reduction. Hence, the four filtering parameters are: (1) search window size in space $W_Q$, (2) spatial block size $W_P$, (3) energy channels used to evaluate pixel similarity E, and (4) filtering strength h.

Figure 2B:
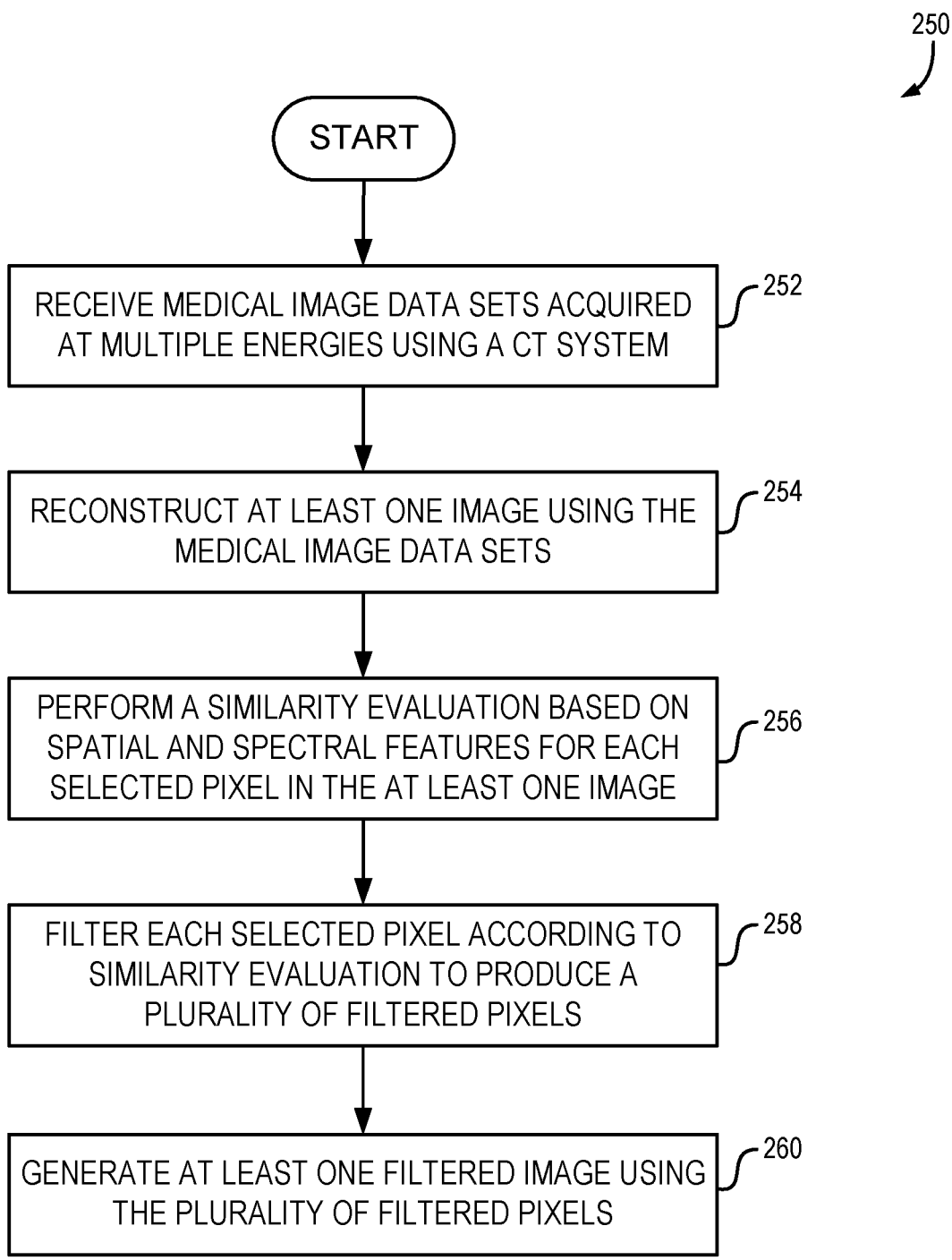
FIG. 2B is another flowchart setting forth steps of a process, in accordance with the present disclosure.

Turning to FIG. 2B, steps of a process 250 in accordance with aspects of the present disclosure are illustrated. The process 250 may be carried out using any suitable system, device or apparatus, such as the system 100 described with reference to FIGS. 1A and 1B. In some aspects, the process 250 may be embodied in a program or software in the form of instructions, executable by a computer or processor, and stored in non-transitory computer-readable media.

The process 250 may begin at process block 252 with receiving or accessing a medical imaging dataset acquired from a subject using a CT system. The imaging dataset may be a two-dimensional (2D), a three-dimensional (3D) or a four-dimensional (4D) multi-energy CT dataset. In particular, the 4D MECT dataset may include a time-resolved series of images, with one or more images in the series being associated with a different time points or time periods. In some implementations, a data acquisition may be performed at process block 252 to acquire the medical imaging dataset.

A reconstruction may then be carried out at process block 254 to generate at least one image. Other processing steps may also be carried out at process block 254. Specifically, one or more patches may be generated for selected pixels in the reconstructed images. In particular, each patch may be defined by at least two spatial dimensions and an energy dimension. For example, a patch may include a 2D set of pixels about a selected pixel that is acquired at multiple energies. To this end, the patch may be assembled as a 3D block, as described with reference to FIG. 4. As described, volumetric and temporal information may also be included, and thus patches or blocks may extend to higher dimensions. For example, a patch may include a 3D set of pixels about a selected pixel that is acquired at multiple energies. To this end, an assembled block may be a 4D block. Temporal information may add another dimension to the block.

Then, at process block 256, a similarity evaluation based on spatial and spectral features may be carried out for each selected pixel in the reconstructed image(s). To do so, as described, a search may be performed using a search window. Patches or assembled blocks may be utilized to determine a similarity between selected pixels and pixels in the search window, in accordance with Eqn. 1. In particular, a summed square difference (SSD) computation may be used in the similarity evaluation that uses spatial and spectral features captured in the assembled blocks. As described, pixels with lower SSD correspond to higher similarity, and vice versa.

Then, a filtering of each selected pixel in the reconstructed image(s) may then be performed according to the similarity evaluation, as indicated by process block 258. As described, a filtered pixel may be obtained using a weighted average of pixels in the search window, wherein pixel weights in the search window are determined based on the similarity evaluation. In some aspects, differences in image noise levels at distinct energy level channels may also be determined and used to adapt the pixel weights. In addition, an optimization process may be carried out to identify a size of the search window, spatial block size, energy channel and filtering strength. As indicated at process block 260, at least one filtered image may then be generated using the plurality of filtered pixels generated at process block 258.

The above-described approach may be performed in an image space, a projection space, or a combination of both. To this end, for instance, medical image data sets may be analyzed to determine spatial information and spectral information, or features. Based on a similarity evaluation performed using such information or features, a filtering of one or more generated images generated from the data may be carried out to generate at least one filtered image. In addition to utilizing a non-local means (NLM) filter, other filters that may utilize spatial and spectral information may be utilized. For example a non-local total variation (TV) filter may be utilized.

The above-described systems and methods may be further understood by way of example. The following example is offered for illustrative purposes only, and is not intended to limit the scope of the present invention in any way. Indeed, various modifications of the invention in addition to those shown and described herein will become apparent to those skilled in the art from the foregoing description and the following example and fall within the scope of the appended claims.

EXAMPLE

The present Multi-Energy Non-Local Means (MENLM) technique uses redundant information in MECT images to achieve noise reduction. In this method, spatio-spectral features were used to determine the similarity between pixels, making the similarity evaluation more robust to image noise. The performance of this MENLM filter was tested on images acquired on a whole-body research photon counting CT system. The impact of filtering on image quality was quantitatively evaluated in phantom studies in terms of image noise level (standard deviation of pixel values), noise power spectrum (NPS), in-plane and cross-plane spatial resolution, CT number accuracy, and subjective low-contrast spatial resolution using the American College of Radiology (ACR) CT accreditation phantom. Clinical feasibility was assessed by performing MENLM on contrast-enhanced swine images and unenhanced cadaver head images using clinically relevant doses and dose rates.

Phantom studies demonstrated that the MENLM filter reduced noise substantially and still preserved the shape and peak frequency of the NPS. With 80% noise reduction, MENLM filtering caused no degradation of high-contrast spatial resolution, as illustrated by the modulation transfer function (MTF) and slice sensitivity profile (SSP). CT number accuracy was also maintained for all energy channels, demonstrating that energy resolution was not affected by filtering. The subjective evaluation using the ACR phantom demonstrated an improvement in low-contrast performance. MENLM achieved effective noise reduction in both contrast-enhanced swine images and unenhanced cadaver head images, resulting in improved detection of subtle vascular structures and the differentiation of white/gray matter.

As will be described, MENLM achieved around 80% noise reduction in MECT images and improved the detection of subtle anatomical and low contrast features, while maintaining spatial and energy resolution. MENLM filtering may improve diagnostic or functional analysis accuracy and facilitate radiation dose and contrast media reduction for MECT.

Image Quality Evaluation of the MENLM Method

To assess the impact of $W_\Omega=11$, $W_P=3, E=4$. filtering on image quality, the proposed MENLM filter was applied to MECT images acquired using a research whole-body PCCT scanner (Siemens Healthcare, Forchheim, Germany). The data were acquired using "chess mode", where data from all 16 sub-pixels of the detector were combined to simultaneously generate 4 threshold-based images by counting photons above different energy thresholds. Three additional bin-based images were derived by subtracting the photon counts between adjacent thresholds. In this implementation of the above-described method, only the four threshold-based images associated were used for the calculation of pixel similarity (and weight), as they represent the original measurements and have lower noise than the bin-based images. Because the pixels at different energy channels are perfectly registered in space and represent the same material, the weight determined from threshold-based data was applied to filter the noisy bin-based images. Universal parameter settings were used for all tests except for the filtering strength h. In the following sections, the effect of h on image noise and spatial resolution is evaluated. From these results, the filtering strength h that is used for the remaining tests is determined.

Evaluation of MENLM Using Phantom Studies

A series of phantom studies were performed to quantitatively evaluate the influence of MENLM filtering on image quality in terms of image noise level, noise power spectrum (NPS), in-plane and cross-plane spatial resolution, energy profile accuracy, and low-contrast resolution. The image noise and NPS were measured using a 20 cm diameter cylindrical phantom filled with water. The acquisition and reconstruction parameters are provided in Table 1.

To test the noise reduction capabilities of one implementation of the above-described technique, the phantom was scanned at two dose levels. Images were reconstructed with a quantitative, medium smooth kernel (D30). The low-dose (25.1 mGy) images were denoised using the MENLM filter with the strength setting h varying from 0.7 to 1.5. A procedure following the general framework described previously was used to calculate a 2D NPS for the three image set: high-dose, low-dose, low-dose with MENLM denoising. A circular average of the 2D NPS was taken to yield a 1D NPS profile.

TABLE 1

Acquisition and Reconstruction Parameters Used to Scan the Phantoms.

| Parameters | Noise & NPS | MTF | SSP | CT # Accuracy | ACR | Pig | Cadaver Head |
|---|---|---|---|---|---|---|---|
| Detector Collimation, mm | | | | 32 × 0.5 | | | |
| Tube potential, kV | | | | 140 | | | |
| Energy thresholds, keV | | | [25, 45, 65, 85] | | | | [20, 50, 63, 83] |
| Tube current, mA | 400/100 | 80 | 140 | 140 | 400 | 540 | 220 |
| Rotation time, s | 1.0 | 0.5 | 0.5 | 1.0 | 0.5 | 0.5 | 1.0 |
| Acquisition FOV, mm | | | | 275 | | | |
| Scan mode | | | | Head | | | |
| Pitch | N/A* | 0.5 | 0.5 | N/A* | 0.6 | 0.6 | 0.6 |
| CTDIvol, mGy | 101.1/25.1 | 10.1 | 17.7 | 35.5 | 50.5 | 68.4 | 55.5 |
| Image thickness, mm | 2.0 | 1.0 | 0.5 | 2.0 | 5.0 | 3.0 | 1.0 |
| Image interval, mm | 0.8 | 1.0 | 0.1 | 0.8 | 1.0 | 2.0 | 1.0 |
| Reconstruction kernel | | | | D30 | | | D40 |
| Reconstruction FOV, mm | 200 | 50 | 50 | 200 | 200 | 275 | 275 |

(*N/A refers to sequential scan.)

The in-plane spatial resolution was evaluated using the modulation transfer function (MTF) measured using a 0.125 mm diameter tantalum wire. The acquisition and reconstruction parameters are also provided in Table 1. Reconstructed images were denoised using the MENLM filter, with filtering strength h set to achieve 30-80% noise reductions. The MTF for both original and filtered images was calculated using methods, such as described in J. M. Boone, "Determination of the presampled MTF in computed tomography," Med Phys 28, 356-360 (2001), which is incorporated herein by reference.

The cross-plane spatial resolution was evaluated using the slice sensitivity profile (SSP), which was measured using a thin gold foil phantom (25 μm thickness) that was embedded inside a tissue-equivalent plastic cylinder with a diameter of 23 mm (QRM, Moehrendorf, Germany). The acquisition and reconstruction parameters are provided in Table 1. Reconstructed images were also denoised using the MENLM filter, with filtering strength h set to achieve 80% noise reduction. For each image, the maximum CT number within a region of interest (ROI) centered over the gold foil was recorded after background subtraction. The SSP was plotted as the normalized CT number as a function of slice location.

The impact of filtering strength h on CT number accuracy was evaluated using scans of $CaCl_2$) and iodinated-contrast-material water solutions, and their mixtures, in a 20 cm semi-anthropomorphic water tank (referred to as calcium and iodine solution phantom). The acquisition and reconstruction parameters are provided in Table 1. Images were denoised using the MENLM filter, again with filtering strength h set to achieve 80% noise reduction. ROIs were drawn on each material sample to measure CT numbers in both threshold- and bin-based images.

The low-contrast resolution was evaluated subjectively using the low-contrast resolution module of the American College of Radiology (ACR) CT accreditation phantom. The acquisition and reconstruction parameters are provided in Table 1. The MENLM filter was applied on the reconstructed images with the filtering strength h set to achieve 80% noise reduction.

Clinical Feasibility Testing

Pig scan: After institutional animal care and use committee approval, one 3-month-old female swine was scanned using a head CT scan protocol. The acquisition and reconstruction parameters are provided in Table 1. Images were denoised using the MENLM filter, with filtering strength h set to achieve 80% noise reduction; the results were compared with the Filtered Back Projection (FBP) images.

Cadaver head scan: With approval of our institutional biospecimen committee, a fresh-frozen human cadaver head was obtained from our institution's department of anatomy. The acquisition and reconstruction parameters are provided in Table 1. Images were reconstructed using a D40 kernel and were denoised using the MENLM filter, with filtering strength h set to achieve 80% noise reduction; the results were compared with the Filtered Back Projection (FBP) images.

Results

Evaluation of MENLM Using Phantom Studies
Image Noise Level and Filtering Strength h By varying the filtering strength h, the amount of noise reduction was determined for all threshold- and bin-based images (Table 2).

TABLE 2

Evaluation of filtering strength h on the amount of noise reduction, where noise reduction was averaged for all threshold- and bin-based images.

| | Filtering Strength (h) | | | | | |
|---|---|---|---|---|---|---|
| | 0.7 | 0.8 | 0.9 | 1.0 | 1.2 | 1.5 |
| Noise Reduction (%) | 36.9 ± 7.7 | 45.9 ± 7.8 | 53.8 ± 7.3 | 60.6 ± 6.5 | 70.4 ± 5.1 | 80.1 ± 3.1 |

Noise Power Spectrum

Figure 5:
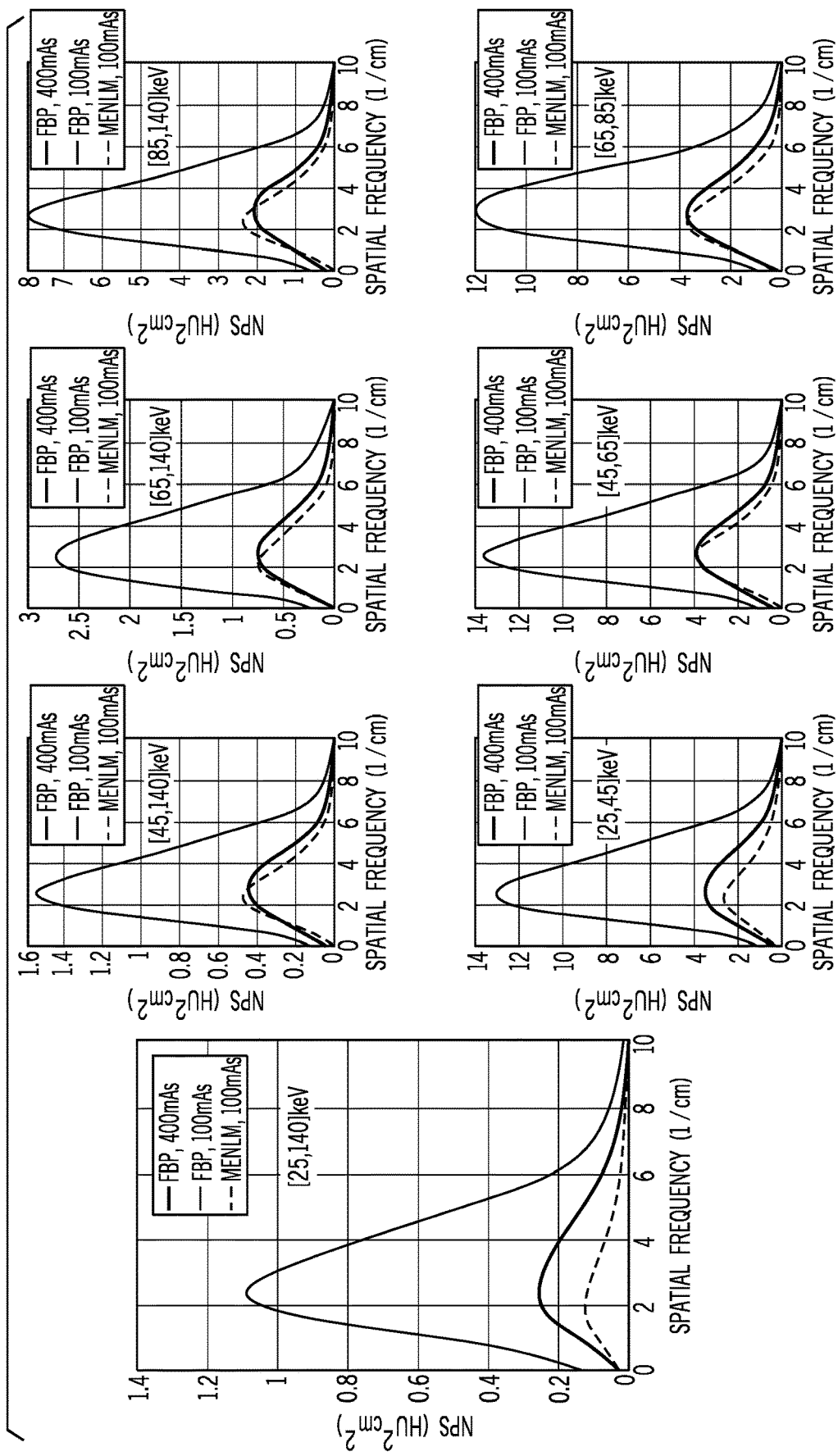
FIG. 5 is a series of correlated graphs showing a comparison of noise power spectra (NPS) between the filtered backprojection (FBP) images and multi-energy nonlocal means (MENLM) filtered images with 50% noise reduction.
Figure 6:
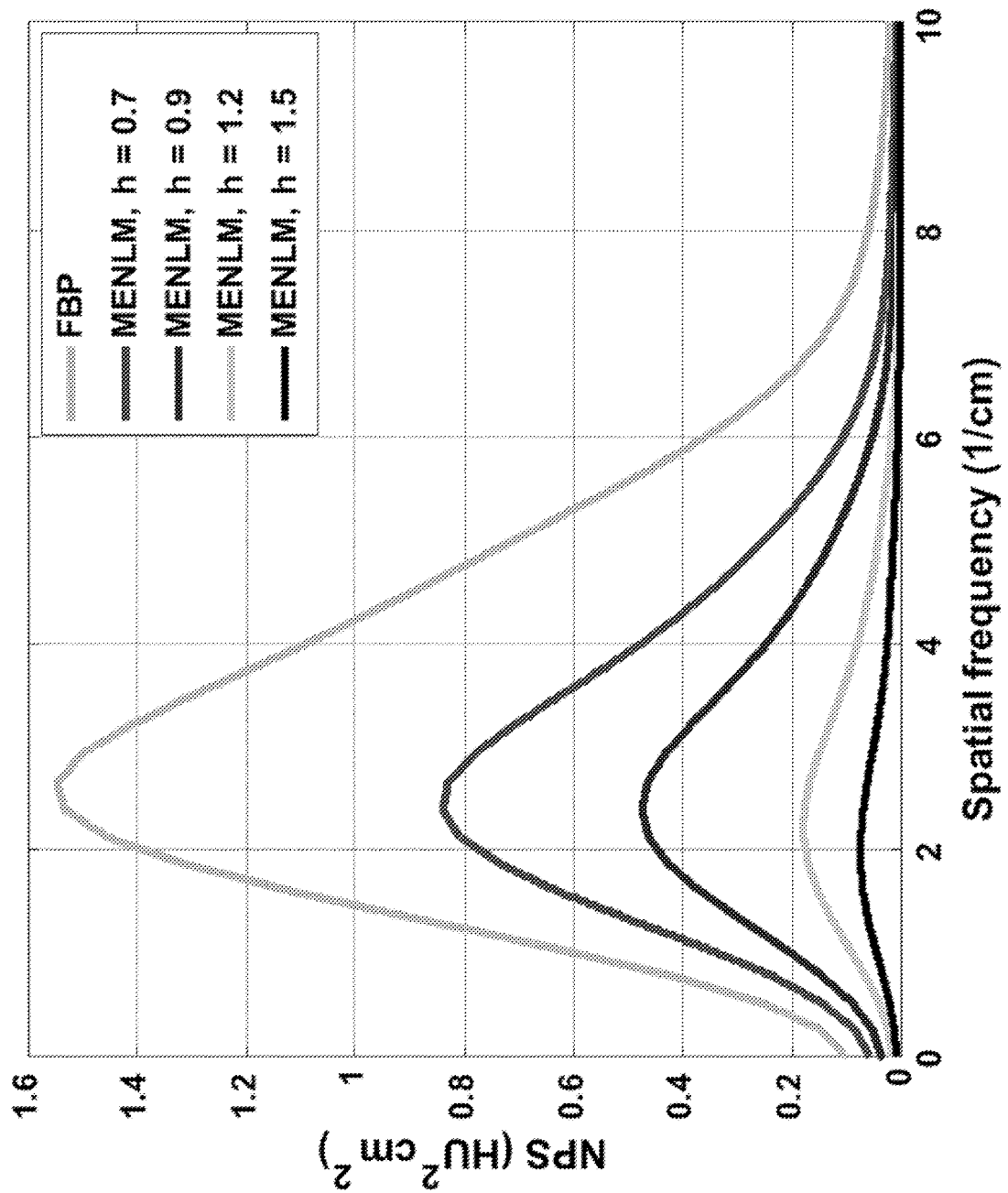
FIG. 6 is a graph showing a dependence of NPS on filtering strength for threshold-based images [45,140 keV].

Specifically, FIG. 5 provides a series of graphs that show that the NPS of the MENLM-filtered (h=0.9) low-dose FBP images generally had similar shapes and magnitudes as those of the high-dose FBP images, but with a noticeable shift of the peak frequency towards lower frequencies. Similar behaviors were observed for all threshold- and bin-based images, except for the threshold- and bin-based images associated with the lowest energy thresholds (e.g. [20,140 keV] and [25.45 keV]). As shown in FIG. 6, the peak frequency tended to shift more towards the lower frequency end with increased filtering strength.

High Contrast Spatial Resolution

Figure 7:
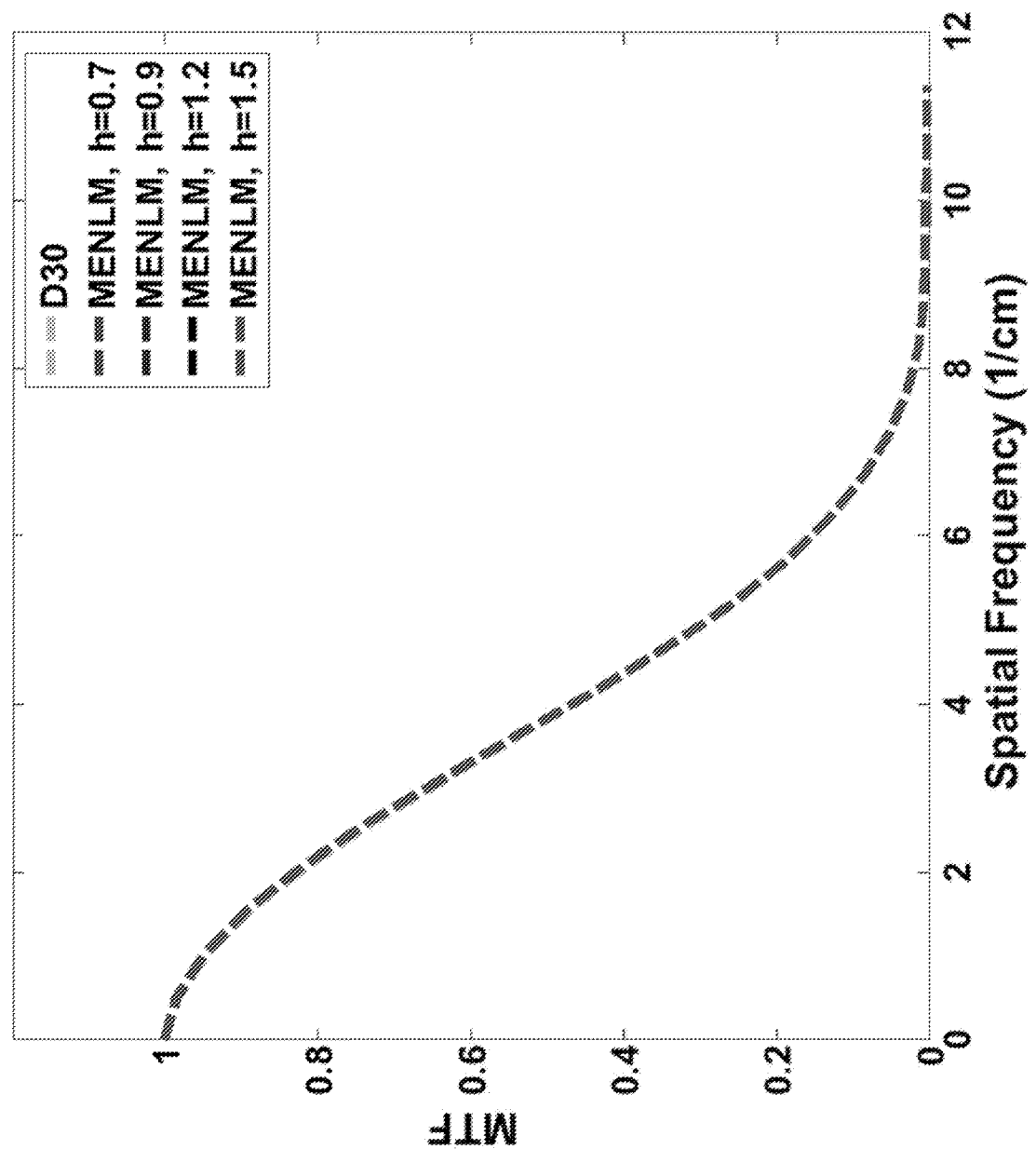
FIG. 7 is a graph showing a dependence of in-plane spatial resolution on filtering strength for Threshold 1 images [25,140 keV].
Figure 8:
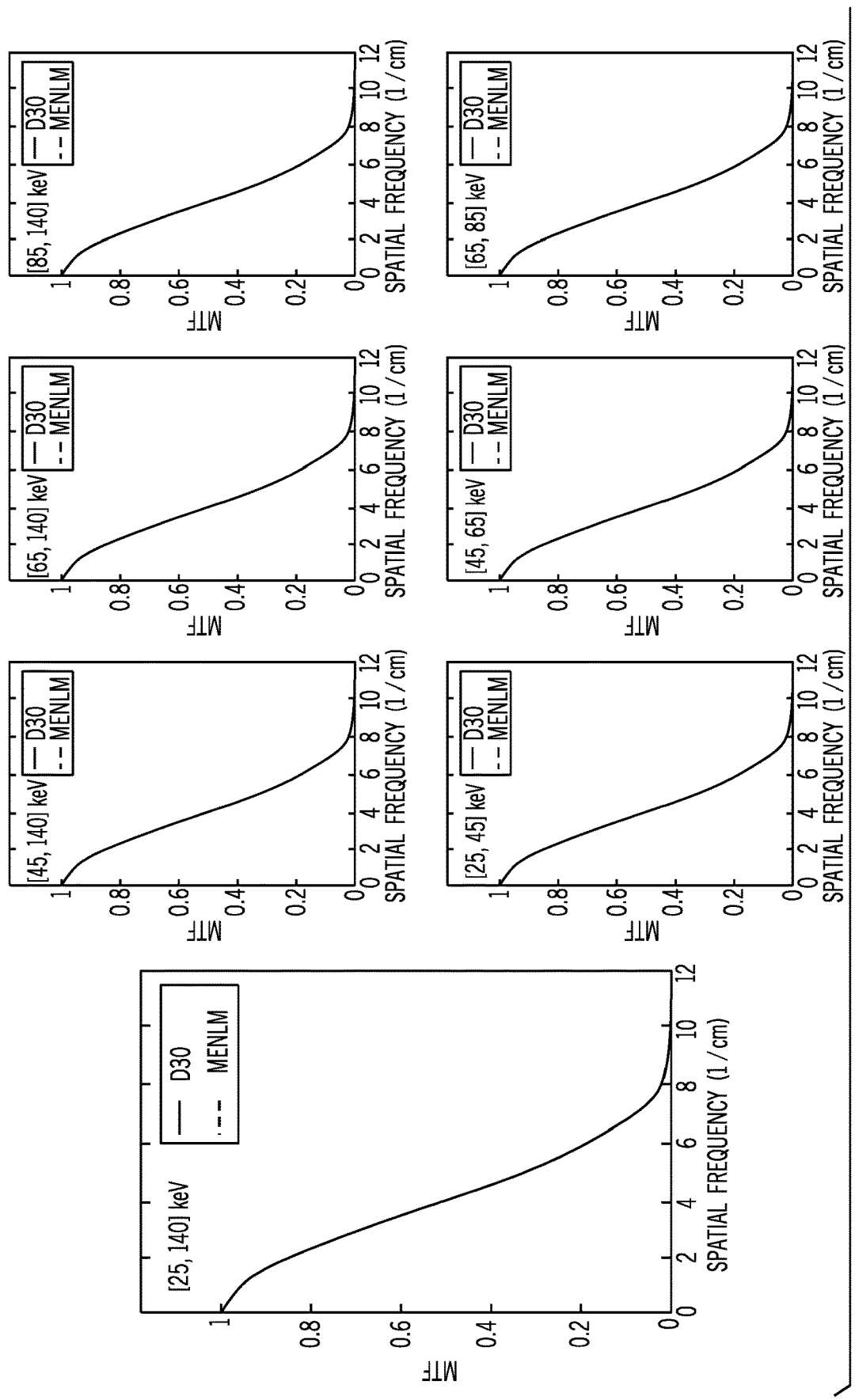
FIG. 8 is a series of correlated graphs showing a comparison of changes in in-plane spatial resolution between a FBP image (D30) and MENLM with 80% noise reduction for all threshold- and bin-based images.
Figure 9:
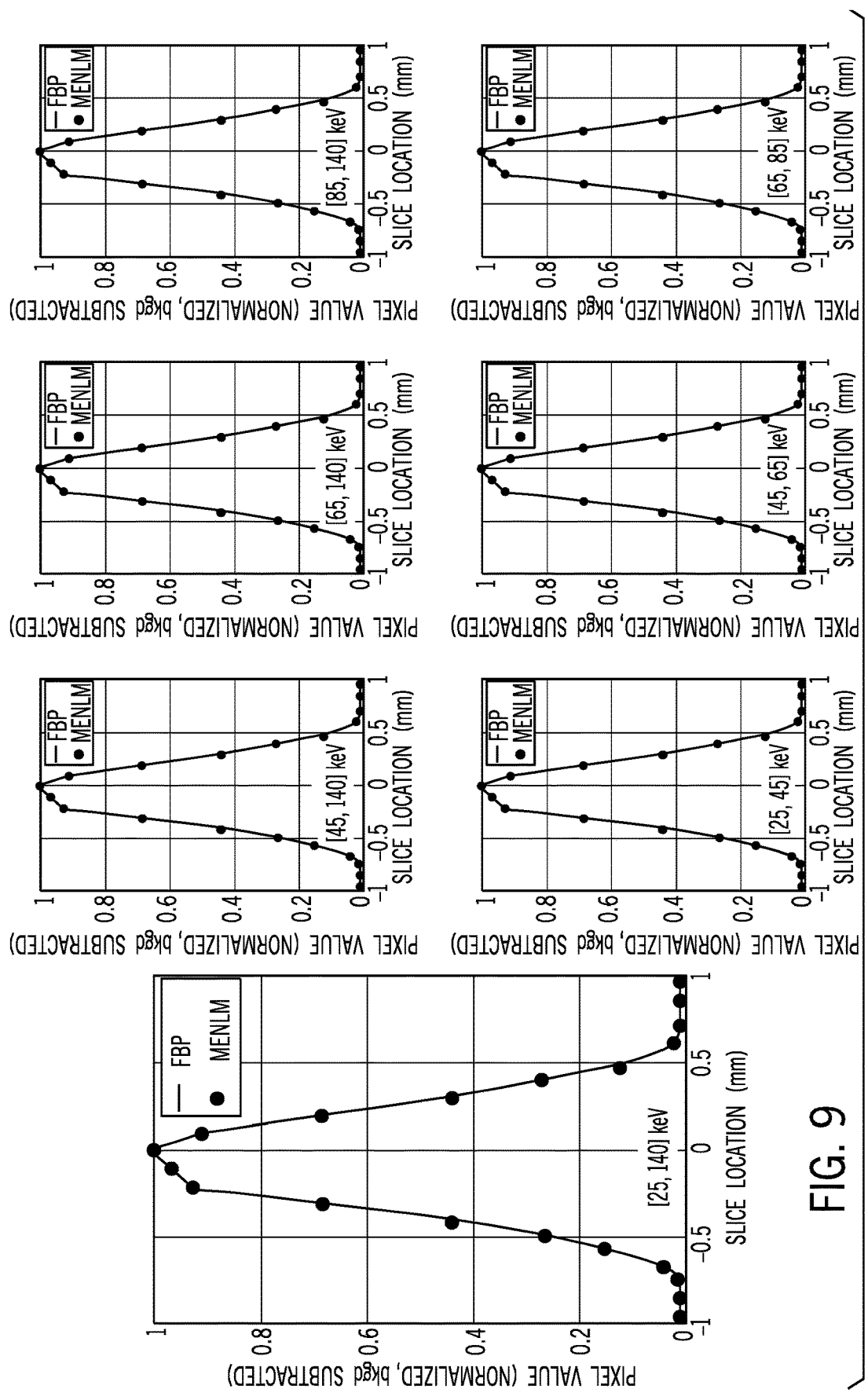
FIG. 9 is a series of correlated graphs showing a comparison of changes in cross-plane spatial resolution between the FBP image and MENLM with 80% noise reduction.

The MTF curves of the images reconstructed with the FBP reconstruction algorithm and MENLM with different filtering strengths h are shown in FIG. 7 for the threshold-based image with the lowest energy threshold. The MTF was essentially unchanged with up to 80% noise reduction (h=1.5), although slight changes were observed in some images with higher noise reduction (data not shown). As best shown in FIG. 8, the same behavior was observed for all other energy threshold-based and bin-based images. Hence, in the following experiments, we adopted a filtering strength of h=1.5 to evaluate the image quality after filtering. The SSPs for both FBP and filtered images are shown in FIG. 9. The SSPs before and after the MENLM filtering did not change, demonstrating that cross-plane spatial resolution was not affected by the filter with 80% noise reduction.

CT #Accuracy

TABLE 3

Evaluation of CT number change with 80% noise reduction for all threshold-based and bin-based images.

| | Energy Range (keV) | | | | | | |
|---|---|---|---|---|---|---|---|
| CT # Change (HU) | [25, 140] | [45, 140] | [65, 140] | [85, 140] | [25, 45] | [45, 65] | [65, 85] |
| Sample 1 | 0.1 | −0.1 | 0.5 | 1.8 | 0.7 | 0.6 | −1.2 |
| Sample 2 | 0.7 | 1.2 | 0.2 | 0.9 | 1.9 | −1.7 | 1.8 |
| Sample 3 | 0.6 | 1.9 | 0.9 | 1.2 | 2.3 | −1.6 | 2.4 |
| Sample 4 | 0.6 | 0.8 | 0.5 | 2.0 | 1.9 | 0.1 | −0.2 |
| Sample 5 | 0.7 | 1.2 | 1.0 | 1.6 | 1.9 | 0.6 | 1.4 |
| Sample 6 | 0.7 | −0.1 | 0.5 | 0.6 | 2.0 | 0.7 | −0.5 |
| Sample 7 | 0.6 | 1.2 | 0.7 | −0.3 | 1.3 | 0.5 | 1.9 |
| Sample 8 | 0.0 | 0.3 | 0.8 | 2.3 | −1.0 | 1.2 | −1.0 |
| Mean | 0.5 | 0.8 | 0.6 | 1.3 | 1.4 | 0.1 | 0.6 |

Figure 10:
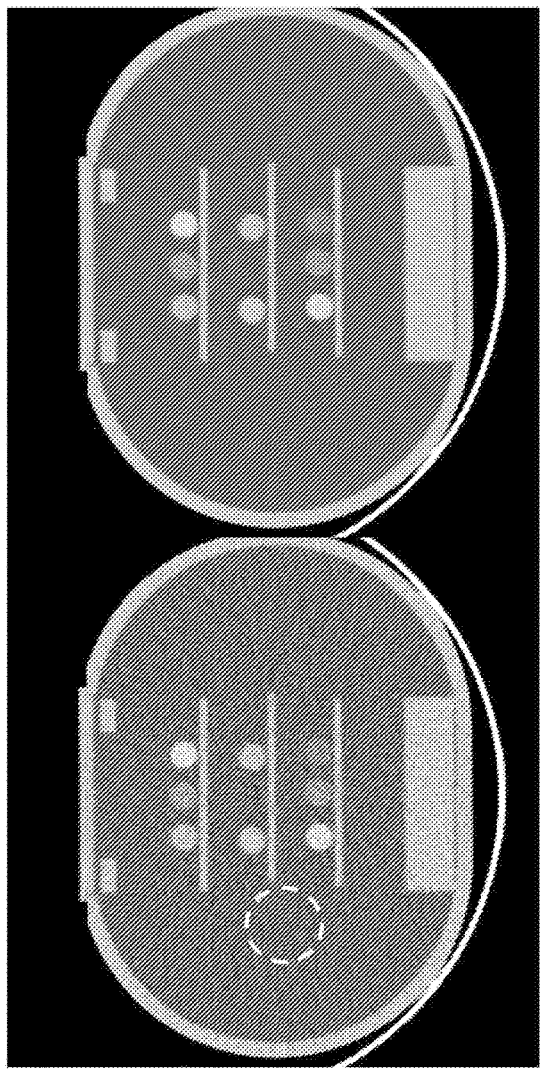
FIG. 10 is a pair of images showing calcium and iodine solution phantoms used for the CT number accuracy evaluation with a FBP image on left and a MENLM image on right. The mean and standard deviation of CT numbers inside the dotted ROI were −0.3±19.2 and −0.4±4.1 HU, respectively. W/L=400/40 HU.

FIG. 10 shows the FBP image of the calcium and iodine water solution phantom and the MENLM filtered image. ROI measurements of all samples demonstrated that the CT number accuracy was well preserved in all threshold- and bin-based images, with maximum differences of only 2.3 HU, as provided in Table 3. This demonstrated that energy resolution was preserved in the MENLM filtered images.

Low Contrast Resolution

Figure 11:
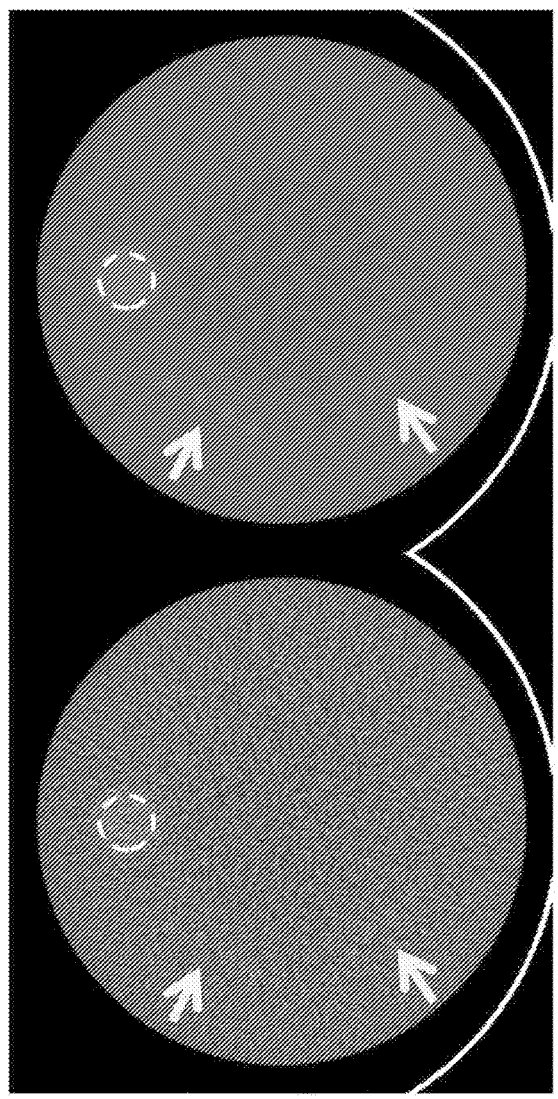
FIG. 11 is a pair of images showing improved low-contrast resolution after MENLM filtering (right) comparing to a FBP image (left). Arrows indicate the locations of low-contrast objects (top: 6 mm rods; Bottom: 5 mm rods). The mean and standard deviation of CT numbers inside the dotted ROI were 99.3±5.5 (left) and 98.6±1.0 HU (right), respectively. W/L=100/100 HU.

FIG. 11 shows the FBP image of the ACR phantom and the MENLM filtered image. In the FBP image, the 6 mm rods are barely visible and the 5 mm rods are totally lost. However, in the MENLM filtered image, all 6 mm and 5 mm rods are clearly visible, indicating improved low contrast resolution with the 80% noise reduction. Measurements showed that the mean CT number values were well maintained in the filtered image.

Clinical Feasibility Testing

Figure 12:
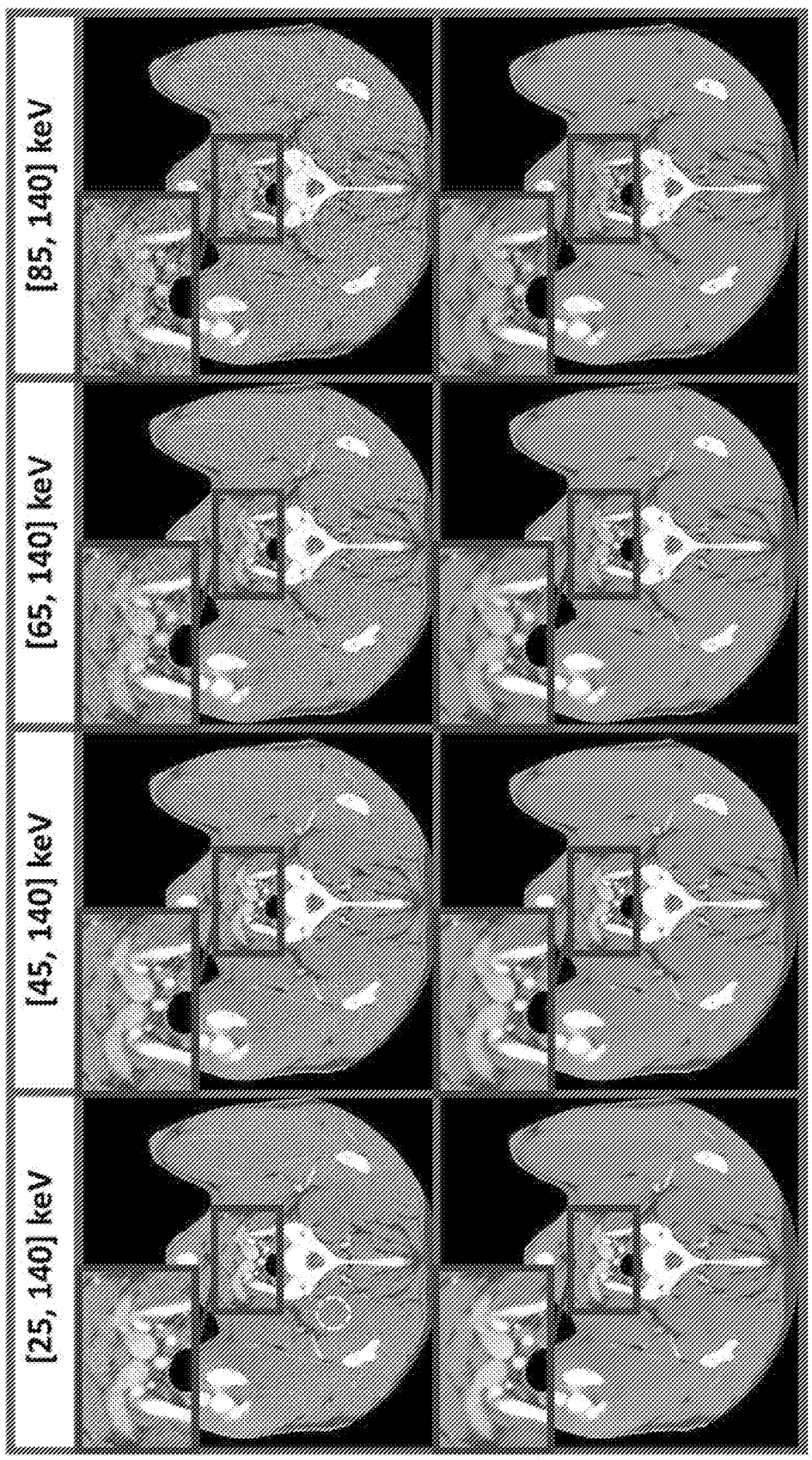
FIG. 12 is a series of correlate images showing that MENLM greatly reduces the noise in threshold-based images without affecting subtle anatomical structure and energy resolution. In original FBP images (top row), the mean and standard deviation of CT number inside the dotted ROI were 59.6±15.1, 59.9±17.2, 62.2±22.2, and 57.9±32.5, respectively. After MENLM filtering (bottom row), the values were 59.5±3.4, 59.5±4.3, 61.5±4.6, and 57.7±7.2, respectively. W/L=400/40 HU.

Pig scan: In the threshold-based pig head images of FIG. 12, MENLM achieved around 80% noise reduction without affecting subtle anatomical structures and energy resolution. This results in enhanced contrast-to-noise ratio in all threshold-based images and improves the differentiation between materials with different composition (e.g. bone and iodinated blood) and/or with different density (e.g. blood vessels with different contrast enhancement).

Figure 13:
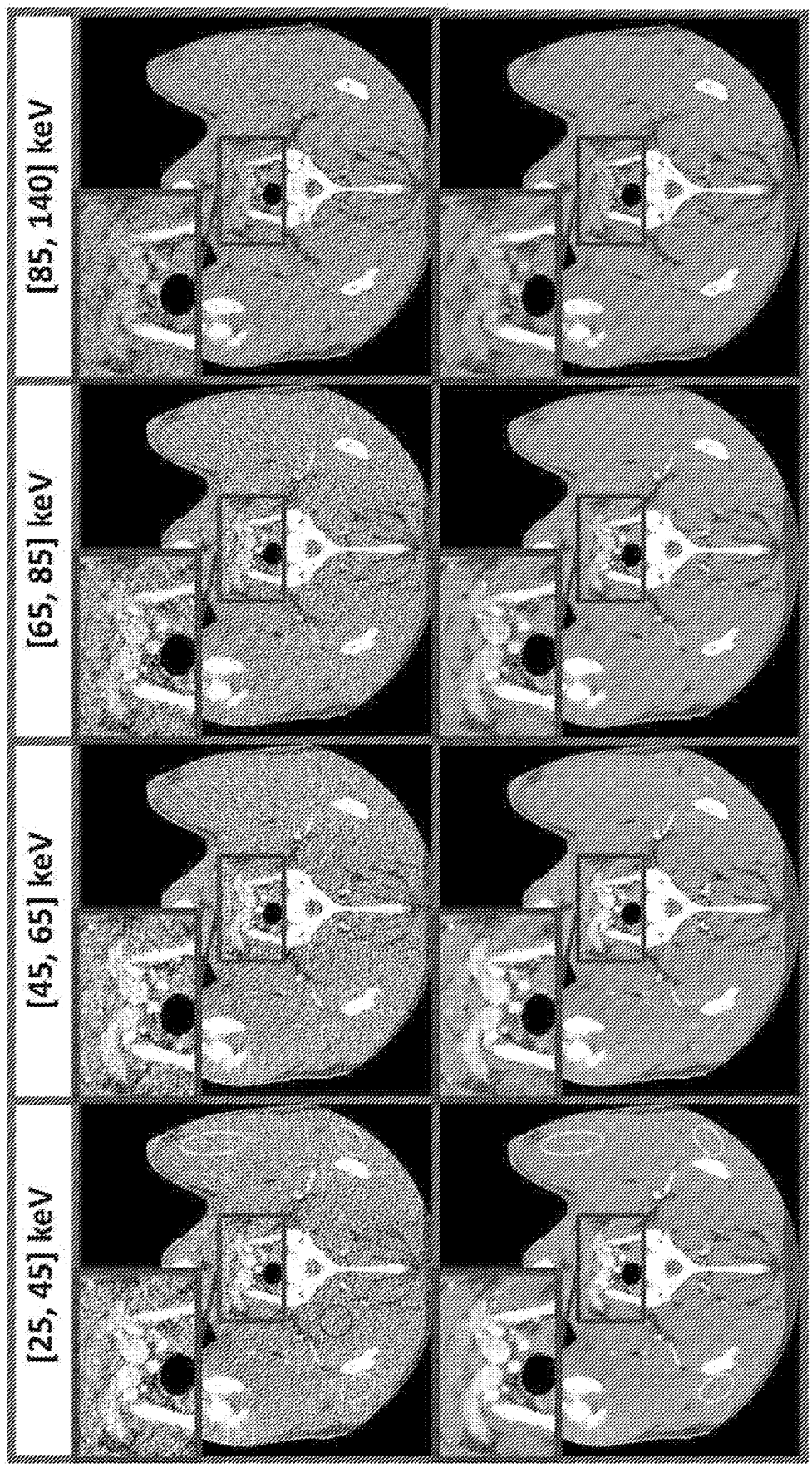
FIG. 13 is a series of images showing bin-based images after MENLM filtering (bottom row) improved the detection of subtle enhanced vessels (yellow ROIs in low-energy bin-based image) and low-contrast structures (Close-ups in high-energy bin-based image). In original FBP images (second row), the mean and standard deviation of CT number inside the red ROI are 62.2±55.6, 62.8±57.8, 67.2±48.8, and 57.9±32.5, respectively. After MENLM filtering, the values are 62.7±9.1, 62.6±10.8, 65.7±9.5, and 57.7±7.2, respectively. W/L=400/40 HU.

In all bin-based images, MENLM greatly reduced image noise and streaking artifacts, making subtle anatomical structure easier to detect. In low-energy bin-based images (FIG. 13, first and second columns, top row), although iodine contrast enhancement is good, small vessels can still be difficult to detect due to the noisy background. After filtering by MENLM, the small vessels are much easier to detect due to the substantial noise reduction (FIG. 13, first and second columns, bottom row). Similarly, in high-energy bin-based images (FIG. 13, last column, top row), reduced calcium blooming effect, one benefit of photon counting CT, can be observed so that surrounding features (such as lumen inside vessels) can be evaluated without being shaded by bone or high density calcification. However, the reduced contrast inside the lumen also makes it difficult to resolve the location and structure of the vessel. After MENLM filtering to control noise, the edge of the vessel can be better resolved with improved CNR and reduced calcium blooming effect (FIG. 13, last column, bottom row).

Figure 14:
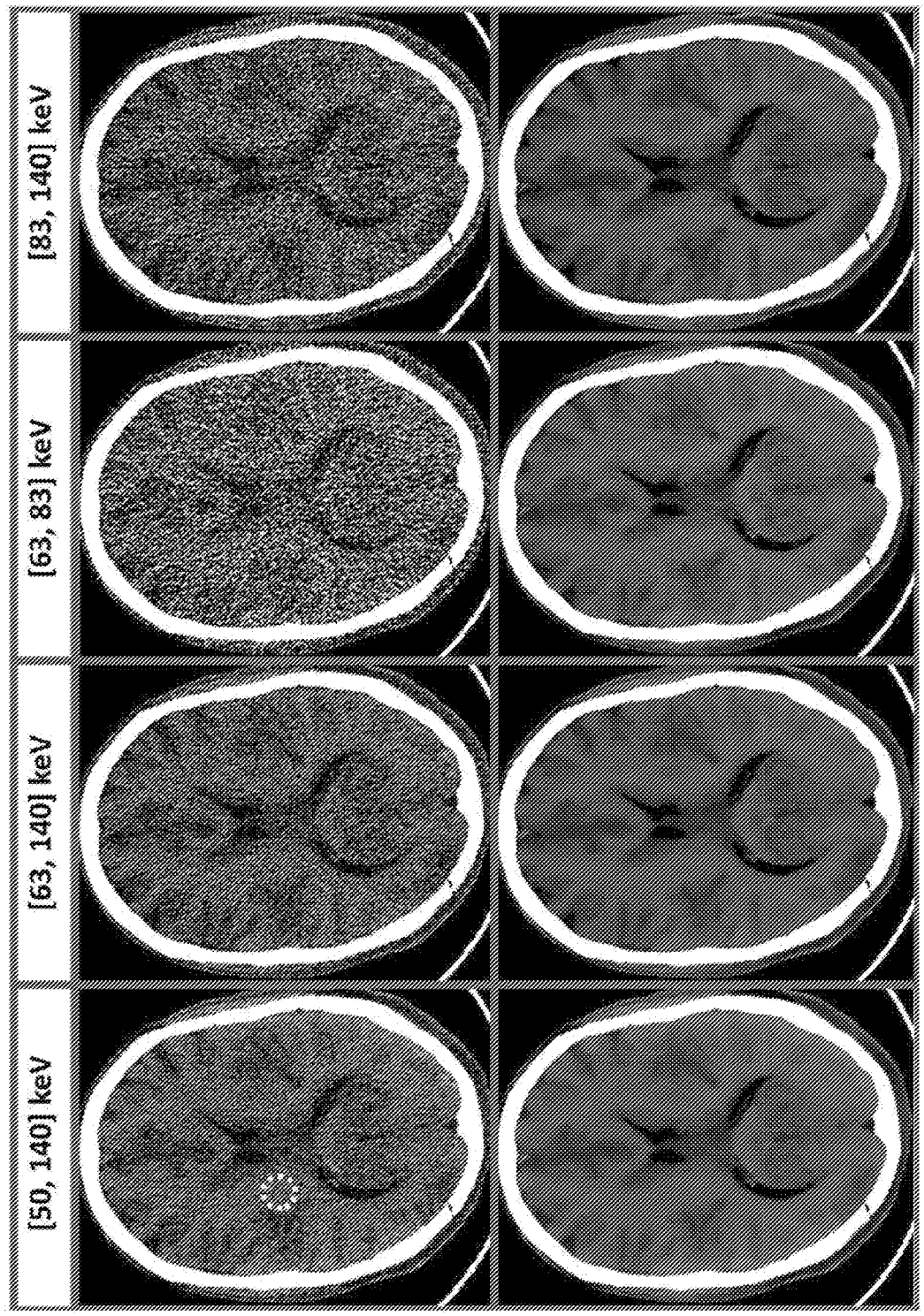
FIG. 14 is a series of images showing MENLM filtering of two noisy threshold-based and two bin-based images (bottom row) from a cadaver head scan demonstrated improved low-contrast resolution. The similarity/weight determined from threshold-based images provided robustness to noise reduction. (In original FBP images (top row), the mean and standard deviation of the CT number in the dotted ROI were −10.7±15.1 HU, −12.5±18.2 HU, −9.8±40.6 HU, and −13.3±31.1 HU, respectively. With MENLM, the values were −11.3±2.4 HU, −13.1±2.3 HU, −10.0±3.7 HU, and −14.3±3.8 HU, respectively.) W/L=150/20 HU.

Cadaver head scan: With MENLM filtering, the noise in both threshold-and bin-based images from the cadaver head scan (FIG. 14) was greatly reduced. This greatly enhanced image quality, as evidenced by the improved differentiation between white and gray matter and conspicuity of subtle structures (such as calcifications).

Discussion

The above results show that the above-described, image-domain, non-iterative noise reduction technique to reduce noise in MECT images that can be implemented efficiently. MECT data may require longer pre-processing, reconstruction, and post-processing time. Iterative and projection-domain approaches to noise reduction tend to prolong the time needed to return the final image for viewing. The above-described systems and methods can process the reconstructed images directly to achieve fast noise reduction, and is convenient since the computation time and the amount of noise reduction can be predetermined.

As demonstrated by the presented results, MENLM can effectively reduce noise by up to 80%, while preserving spatial and energy resolution and improving low contrast resolution. This substantially improves the signal to noise ratio in the image, especially for narrow energy bin-based images, which are associated with high noise levels. Previously, we have reported that decreased beam hardening and calcium blooming were observed in high-energy bin-based images and increase contrast enhancement of higher atomic number materials in the low-energy bin-based images. High-energy bin-based images with reduced calcium blooming might improve the accuracy of luminal stenosis quantification, whereas low-energy bin-based images with higher contrast may benefit detection of subtle anatomical structures, such as iodine-filled coronary arteries. However, higher image noise in a narrower energy bin-based image may offset these benefits, especially for the detection of subtle structures, such as small arteries and calcifications. With MENLM filtering, the noise is substantially reduced and the improved contrast to noise ratio in energy bin-based images may benefit such tasks, as evidenced by the pig scan and cadaver head results.

The reduced noise and preserved spatial and energy resolution may potentially benefit a series of clinical applications of MECT. Material decomposition, for example, is a primary application of MECT to separate or quantify basis materials from a mixture. However, material decomposition is notorious for its noise magnification, such that basis material images can be too noisy for clinical use. MENLM effectively reduced noise without affecting energy resolution, such that the noise levels in the processed images after material decomposition may be adequate to meet clinical requirements. Additionally, the reduction in noise levels may be traded for a large reduction in iodinated contrast usage or radiation dose. Also, this technique can also be used to the benefit of image processing techniques (segmentation, classification, etc.) performed on multi-energy CT images.

An 80% noise reduction with maintained signal fidelity implies a potential 25-fold radiation dose reduction capability when MENLM is used to maintain image quality. However, slight changes of noise texture (or NPS) were observed in the filtered images (FIGS. 5 and 6) and this might affect some relevant clinical tasks.

CONCLUSION

Thus, the present disclosure provides an approach to practically and effectively achieve substantial noise reduction for MECT images. The proposed MENLM filter reduced image noise in MECT data by as much as 80% without degrading spatial and energy resolution, while improving low contrast resolution.

The present invention has been described in accordance with the embodiments shown, and one of ordinary skill in the art will readily recognize that there could be variations to the embodiments, and any variations would be within the spirit and scope of the present invention. For example, while above-described embodiments employed a map of local noise level as the basis for a denoising filter, the local noise spatial correlation can also be analytically derived and used for the purposes of denoising process. Accordingly, the adaptive filtering can be implemented based on local noise spatial correlation. Accordingly, many modifications may be made by one of ordinary skill in the art without departing from the spirit and scope of the appended claims.

The invention claimed is:

1. A method for producing computed tomography (CT) images, the method including steps comprising:
   (i) obtaining medical image data sets acquired from a subject at multiple energies of irradiating radiation;
   (ii) analyzing the medical image data sets for spatial and spectral features;
   (iii) comparing the spatial and spectral features of the medical image data sets across the multiple energies to identify similarities by:
   forming spatio-spectral blocks from the medical image data sets, each spatio-spectral block comprising a spatial patch centered on a pixel and stacked across each of the multiple energies;
   calculating similarities between different ones of the spatio-spectral blocks; and
   (iv) using the similarities, weighting pixels in the medical image data sets to generate images of the subject having reduced noise compared to images of the subject produced from the medical image data sets without weighting.

2. The method of claim 1 wherein step (i) includes reconstructing multi-energy images of the subject and step (ii) includes applying a non-local means (NLM) filter to search for similar pixels in the multi-energy images.

3. The method of claim 2 wherein step (iv) includes performing a weighted average of pixels identified in step (iii) as similar.

4. The method of claim 3 wherein step (iii) includes quantifying a similarity between pixels using a summed square difference (SSD) relative to spatial and spectral features, wherein pixels with lower SSD correspond to higher similarity.

5. The method of claim 4 wherein pixels with higher similarity are weighted heavier in step (iv) and spatial and energy resolutions are maintained.

6. The method of claim 1 wherein step (iii) includes determining differences in image noise levels at distinct energy level channels and adapting weighting according to the noise levels.

7. The method of claim 1, wherein calculating the similarities between different ones of the spatio-spectral blocks in step (iii) is performed in an image space, a projection space, or both.

8. A computed tomography (CT) imaging system comprising:
   at least one x-ray source configured to emit x-rays at one or more energy levels toward an object to be imaged;
   at least one detector configured to receive x-rays that are attenuated by the object;

a data acquisition system (DAS) connected to the at least one detector to receive an indication of received x-rays at multiple energy levels;

a computer system coupled to the DAS to receive the indication of the received x-rays at multiple energy levels and programmed to:
  (i) obtain medical image data sets acquired from a subject using the multiple energies of irradiating radiation;
  (ii) analyze the medical image data sets for spatial and spectral features;
  (iii) compare the spatial and spectral features of the medical image data sets across the multiple energy levels to identify similarities by:
    forming spatio-spectral blocks from the medical image data sets each spatio-spectral block comprising a spatial patch centered on a pixel and stacked across each of the multiple energies;
    calculating similarities between different ones of the spatio-spectral blocks; and
  (iv) use the similarities, weighting pixels in the medical image data sets to generate images of the subject having reduced noise compared to images of the subject produced from the medical image data sets without weighting.

9. The CT imaging system of claim 8 wherein step (i) includes reconstructing multi-energy images of the subject and step (ii) includes applying a non-local means (NLM) filter to search for similar pixels in the multi-energy images.

10. The CT imaging system of claim 9 wherein step (iv) includes performing a weighted average of pixels identified in step (iii) as similar.

11. The CT imaging system of claim 10 wherein step (iii) includes quantifying a similarity between pixels using a summed square difference (SSD) relative to spatial and spectral features, wherein pixels with lower SSD correspond to higher similarity.

12. The CT imaging system of claim 11 wherein pixels with higher similarity are weighted heavier in step (iv).

13. The CT imaging system of claim 8 wherein step (iii) includes determining differences in image noise levels at distinct energy level channels and adapting weighting according to the noise levels.

14. The CT imaging system of claim 8, wherein the computer system is programmed to calculate the similarities between different ones of the spatio-spectral blocks in an image space, a projection space, or both.

* * * * *